US008383810B2

(12) United States Patent
Thiruvengadam et al.

(10) Patent No.: US 8,383,810 B2
(45) Date of Patent: Feb. 26, 2013

(54) PROCESS FOR THE SYNTHESIS OF AZETIDINONES

(75) Inventors: Tiruvettipuram K. Thiruvengadam, Kendall Park, NJ (US); John S. Chiu, Parsippany, NJ (US); Xiaoyong Fu, Edison, NJ (US); Timothy L. McAllister, Philadelphia, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/323,366

(22) Filed: Dec. 12, 2011

(65) Prior Publication Data

US 2012/0083601 A1   Apr. 5, 2012

Related U.S. Application Data

(63) Continuation of application No. 13/008,458, filed on Jan. 18, 2011, now abandoned, which is a continuation of application No. 11/305,926, filed on Dec. 19, 2005, now abandoned.

(60) Provisional application No. 60/637,594, filed on Dec. 20, 2004.

(51) Int. Cl.
  *C07D 205/08*   (2006.01)
  *C07H 7/02*   (2006.01)
(52) U.S. Cl. .................................... 540/200; 536/29.11
(58) Field of Classification Search .................. 540/200; 536/29.11
See application file for complete search history.

(56) References Cited

U.S. PATENT DOCUMENTS

| 5,728,827 | A | 3/1998 | Thiruvengadam et al. |
| 5,856,473 | A | 1/1999 | Shankar |
| 6,093,812 | A | 7/2000 | Thiruvengadam et al. |
| 6,207,822 | B1 | 3/2001 | Thiruvengadam et al. |
| 6,992,067 | B2 | 1/2006 | Glombik et al. |
| 2007/0049748 | A1 | 3/2007 | Uppala et al. |
| 2008/0032964 | A1 | 2/2008 | Kansal et al. |

FOREIGN PATENT DOCUMENTS

| EP | 0 707 567 | 9/2001 |
| WO | 95/01961 | 1/1995 |
| WO | 97/16424 | 5/1997 |
| WO | 00/34240 | 6/2000 |
| WO | 2006/116499 | 11/2006 |
| WO | 2006/127893 | 11/2006 |
| WO | 2006/137080 | 12/2006 |
| WO | 2007/072088 | 6/2007 |

OTHER PUBLICATIONS

Miyachi, "Use of copper(I) trifluoromethanesulfonate . . . ", J. Org. Chem. (1989), vol. 54, pp. 3511-3513.
Perlmutter, "Diastereoselection in the nucleophilic conjugate . . . ", Tetrahedron Letters (1988), vol. 29, pp. 949-952.
"Silane" <http://en.wikipedia.org/wiki/Silane> downloaded from the internet Feb. 20, 2009.
International Search Report for PCT/US2005/045901, mailed May 23, 2006; 3 pages.
Int'l Preliminary Report on Patentability with Written Opinion for PCT/US2005/045901, mailed Jun. 26, 2007; 6 pages.

*Primary Examiner* — Mark Berch
(74) *Attorney, Agent, or Firm* — Carol S. Quagliato; Catherine D. Fitch

(57) ABSTRACT

A process is provided for preparing azetidinones useful as intermediates in the synthesis of penems and as hypocholesterolemic agents, comprising reacting a β-(substituted-amino)amide, a β-(substituted-amino)acid ester, or a β-(substituted-amino)thiolcarbonic acid ester with a silylating agent and a cyclizing agent selected from the group consisting of alkali metal carboxylates, quaternary ammonium carboxylates, quaternary ammonium hydroxides, quaternary ammonium alkoxides, quaternary ammonium aryloxides and hydrates thereof, or the reaction product of: (i) at least one quaternary ammonium halide and at least one alkali metal carboxylate; or (ii) at least one quaternary ammonium chloride, quaternary ammonium bromide, or quaternary ammonium iodide and at least one alkali metal fluoride, wherein a quaternary ammonium moiety of the cyclizing agent is unsubstituted or substituted by one to four groups independently selected from the group consisting of alkyl, arylalkyl and arylalkyl-alkyl.

32 Claims, No Drawings

PROCESS FOR THE SYNTHESIS OF AZETIDINONES

CROSS-REFERENCE TO RELATED APPLICATIONS

The present application claims priority of U.S. Provisional Application No. 60/637,594 filed Dec. 20, 2004, which application is incorporated by reference herein in its entirety.

BACKGROUND OF THE INVENTION

Field of the Invention

The present invention relates to a process for producing azetidinone or β-lactam compounds useful for treating vascular and lipidemic conditions, as well as intermediates for the synthesis of penems.

Azetidinones are useful as hypocholesterolemic agents, as disclosed in US RE 37,721, and also are useful as intermediates in the synthesis of penems, a known group of antibacterials.

EP Patent No. 0 707 567 discloses processes for preparing azetidinones by reacting a silylating agent and a fluoride ion catalyst cyclizing agent with a suitably protected β-(substituted-amino)amide, a β-(substituted-amino)acid ester, or a β-(substituted-amino)thiolcarbonic acid ester.

U.S. Pat. No. 6,207,822 discloses a process for making the compound (ezetimibe):

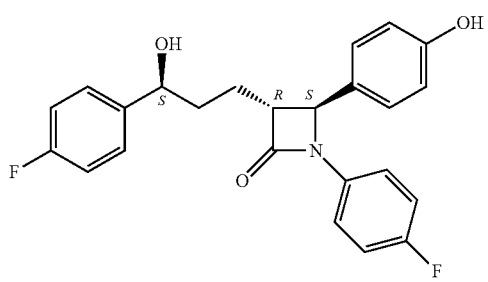

comprising:

(a) reacting p-fluorobenzoylbutyric acid with pivaloyl chloride and acylating the product with a chiral auxiliary to obtain a ketone:

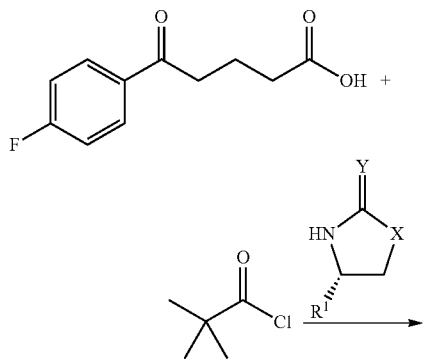

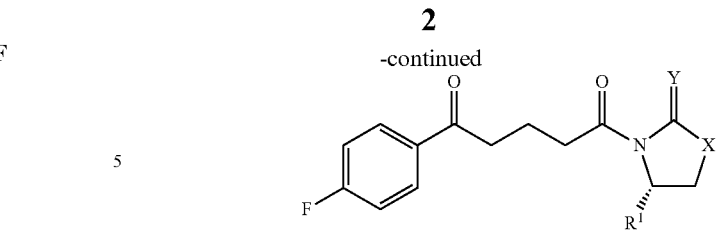

wherein X is —O—, —S— or —N($C_1$-$C_6$ alkyl); Y is =O or =S; and $R^1$ is $C_1$-$C_6$ alkyl, phenyl, naphthyl, substituted phenyl, substituted naphthyl, $C_1$-$C_6$ alkoxycarbonyl or benzyl, wherein the substituents on phenyl and naphthyl are 1-3 substituents selected from the group consisting of $C_1$-$C_6$ alkyl, phenyl and benzyl;

(b) reducing the ketone in the presence of a chiral catalyst to an alcohol;

(c) reacting the chiral alcohol of step (b), an imine and a silyl protecting agent, then condensing the protected compounds to obtain a β-(substituted-amino)amide:

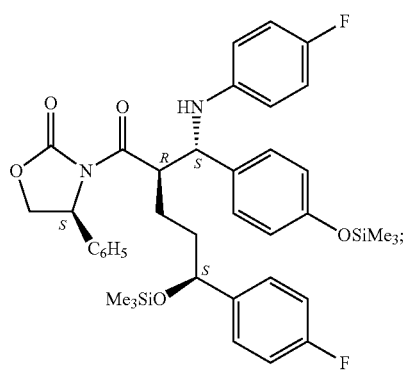

(d) cyclizing the β-(substituted-amino)amide with
(i) a silylating agent and a fluoride ion catalyst cyclizing agent;
(ii) a silylating agent and a quaternary ammonium salt of a chiral auxiliary of step (a); or
(iii) a strong non-nucleophilic base; to obtain the compound:

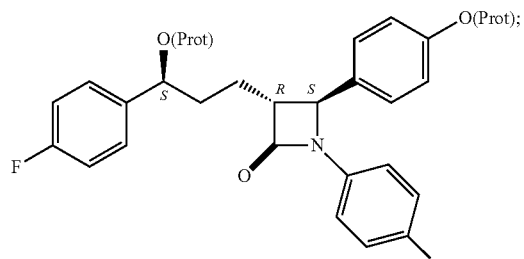

and removing the protecting groups.

Despite the above valuable improvements in preparing azetidinones, there remains a need for alternative, simpler and less expensive processes for preparing azetidinone and β-lactam compounds.

SUMMARY OF THE INVENTION

In one embodiment, the present invention provides a process for preparing an azetidinone, or pharmaceutically acceptable salts, solvates, and prodrugs thereof, comprising the step of reacting:

(1) a β-(substituted-amino)amide, a β-(substituted-amino)-acid ester, or a β-(substituted-amino)thiolcarbonic acid ester with
(2) at least one silylating agent and
(3) at least one cyclizing agent which is
(a) selected from the group consisting of alkali metal carboxylates, quaternary ammonium carboxylates, quaternary ammonium hydroxides, quaternary ammonium alkoxides, quaternary ammonium aryloxides and hydrates thereof, or
(b) the reaction product of:
(i) at least one quaternary ammonium halide and at least one alkali metal carboxylate; or
(ii) at least one quaternary ammonium chloride, quaternary ammonium bromide, or quaternary ammonium iodide and at least one alkali metal fluoride,
wherein a quaternary ammonium moiety of the cyclizing agent is unsubstituted or substituted by one to four groups independently selected from the group consisting of alkyl, arylalkyl and arylalkyl-alkyl.

Another aspect of the present invention is a process for preparing a compound represented by the Formula (IV):

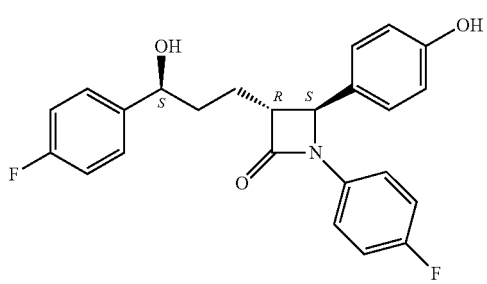

IV comprising the steps of:
cyclizing the β-(substituted-amino)amide of formula XII

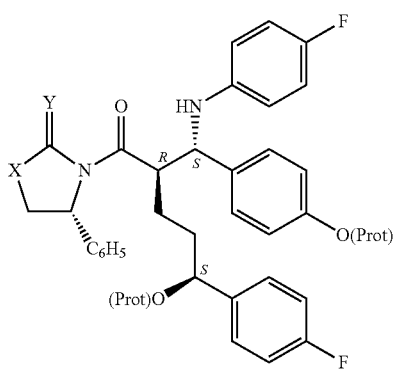

XII wherein X is —O—, —S— or —N($C_1$-$C_6$ alkyl); Y is =O or =S; and $R^1$ is alkyl, aryl or alkoxycarbonyl, and wherein Prot is a silyl protecting group
with at least one silylating agent and at least one cyclizing agent which is
(a) selected from the group consisting of alkali metal carboxylates, quaternary ammonium carboxylates, quaternary ammonium hydroxides, quaternary ammonium alkoxides, quaternary ammonium aryloxides and hydrates thereof, or
(b) the reaction product of:
(i) at least one quaternary ammonium halide and at least one alkali metal carboxylate; or
(ii) at least one quaternary ammonium chloride, quaternary ammonium bromide, or quaternary ammonium iodide and at least one alkali metal fluoride,
wherein a quaternary ammonium moiety of the cyclizing agent is unsubstituted or substituted by one to four groups independently selected from the group consisting of alkyl, arylalkyl and arylalkyl-alkyl,
to obtain the compound of Formula XI:

XI

XI and removing the silyl protecting groups to form the compound of Formula (IV).

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

In its many embodiments, the present invention provides a novel process for preparing azetidinones or β-lactams which can be useful as hypocholesterolemics or as intermediates in the synthesis of penems, a known group of antibacterials.

This process is applicable for preparing azetidinones which are optionally mono-, di- or unsubstituted at each of the C-3 and C-4 positions and substituted at the ring nitrogen. The stereochemistry of C-3, C-4-disubstituted azetidinones prepared by this process is dependent on the starting material: racemic, stereospecific or enantiomeric compounds can be obtained when the corresponding starting materials are used. In particular, this process is useful for the stereospecific preparation of azetidinones substituted in the C-3 and C-4 positions, and optionally substituted at the ring nitrogen.

The processes of the present invention can be used to prepare azetidinones such as are represented by the structural formula (I):

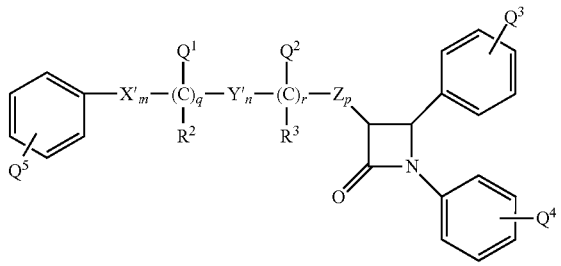

(I)

or pharmaceutically acceptable salts or solvates of the azetidinone of Formula (I), wherein in Formula (I) above:

X', Y' and Z can be the same or different and each is independently selected from the group consisting of —$CH_2$—, —CH(alkyl)- and —$C(alkyl)_2$-;

$Q^1$ and $Q^2$ can be the same or different and each is independently selected from the group consisting of H, —($C_0$-$C_{30}$ alkylene)-G, —$OR^6$, $OC(O)R^6$, —$OC(O)OR^9$, and —$OC(O)NR^6R^7M$;

$Q^3$ is 1 to 5 substituents independently selected from the group consisting of acyl, alkyl, alkylaryl, alkylheteroaryl, alkylsulfonyl alkenyl, alkoxy, alkoxycarbonyl, alkynyl, —($C_0$-$C_{30}$ alkylene)-G, —($C_0$-$C_{10}$ alkylene)-$OR^6$, —($C_0$-$C_{10}$ alkylene)-$C(O)R^6$, —($C_0$-$C_{10}$ alkylene)-$C(O)OR^6$, —($C_0$-$C_{10}$ alkylene)-$OC(O)R^6$, —($C_0$-$C_{10}$ alkylene)-$OC(O)OR^9$, —CH=CH—$C(O)R^6$, —CH=CH—$C(O)OR^6$, —C≡c—$C(O)OR^6$, —C≡C—$C(O)R^6$, —O—($C_1$-$C_{10}$ alkylene)-$OR^6$, —O—($C_1$-$C_{10}$ alkylene)-$C(O)R^6$, —O—($C_1$-$C_{10}$ alkylene)-$C(O)OR^6$, —CN, —C(=N—CN)—$NH_2$, —C(=NH)—$NHR^{10}$, —O—($C_1$-$C_{10}$ alkylene)-$C(O)NR^6R^7$, —O—($C_0$-$C_{10}$ alkylene)-$C(O)NR^6NR^7C(O)OR^6$, —O—($C_1$-$C_{10}$ alkylene)-C(O)(aryl)-N—N=$N^-$, —OC(O)—($C_1$-$C_{10}$ alkylene)-$C(O)OR^6$, —($C_0$-$C_{10}$ alkylene)-$C(O)NR^6R^7$, —($C_0$-$C_{10}$ alkylene)-$OC(O)NR^6R^7$, —$NO_2$, —($C_0$-$C_{10}$ alkylene)-$NR^6R^7$, —O—($C_2$-$C_{10}$ alkylene)-$NR^6R^7$, —$NR^6C(O)R^7$, —$NR^6C(O)OR^9$, —$NR^6C(O)NR^7R^8$, —$NR^6S(O)_{0-2}R^9$, —$N(S(O)_{0-2}R^9)_2$, —$CHNOR^6$, —$C(O)NR^6R^7$, —$C(O)NR^6NR^6R^7$, —$S(O)_{0-2}NR^6R^7$, —$S(O)_{0-2}R^9$, —O—C(O)—($C_1$-$C_{10}$ alkylene)-$C(O)NR^6R^7$, —OC(O)—($C_1$-$C_{10}$ alkylene)-$NR^6C(O)O$—(alkylaryl), —$P(O)(OR^{10})_2$, —($C_1$-$C_{10}$ alkylene)-$OSi(alkyl)_3$, —$CF_3$, —$OCF_3$, halo, alkoxyalkoxy, alkoxyalkoxyalkoxy, alkoxycarbonylalkoxy, alkoxyarylalkoxy, alkoxyiminoalkyl, alkyldioyl, ally, allyloxy, aryloxycarbonyl, aralkoxycarbonyl (arylalkoxycarbonyl), aryl, arylalkyl(aralkyl), aryloxy, arylsulfonyl arylalkoxy, aroyl, aroyloxy, aroylaroyloxy, benzoylbenzoyloxy, carboxy, cyano, cycloalkyl, cycloalkylalkyl, cycloalkenyl, cycloalkenylalkyl, heteroaryl, heteroarylalkenyl, heteroarylalkynyl, heteroarylalkyl, heteroarylalkoxy, heteroarylsulfonyl, heteroarylthio, dioxolanyl, heterocyclyl, heterocyclylalkyl, heterocyclylcarbonyl, heterocyclylcarbonylalkoxy, hydroxy, hydroxyalkyl, alkylsulfonyl, and ring substituents comprising a moiety replacing one available hydrogen atom on a ring system or simultaneously replacing two available hydrogens on adjacent carbon atoms on a ring system as defined below;

$Q^4$ is 1 to 5 substituents independently selected from the group consisting of acyl, alkyl, alkylaryl, alkylheteroaryl, alkylsulfonyl alkenyl, alkoxy, alkoxycarbonyl, alkynyl, —($C_0$-$C_{30}$ alkylene)-G, —($C_0$-$C_{10}$ alkylene)-$OR^6$, —($C_0$-$C_{10}$ alkylene)-$C(O)R^6$, —($C_0$-$C_{10}$ alkylene)-$C(O)OR^6$, —($C_0$-$C_{10}$ alkylene)-$OC(O)R^6$, —($C_0$-$C_{10}$ alkylene)-$OC(O)OR^9$, —CH=CH—$C(O)R^6$, —CH=CH—$C(O)OR^6$, —C≡C—$C(O)OR^6$—C≡C—$C(O)R^6$, —O—($C_1$-$C_{10}$ alkylene)-$C(O)OR^6$, —O—($C_1$-$C_{10}$ alkylene)-$C(O)R^6$, —O—($C_1$-$C_{10}$ alkylene)-$C(O)OR^6$, —CN, —C(=N—CN)—$NH_2$, —C(=NH)—$NHR^{16}$, —O—($C_1$-$C_{10}$ alkylene)-$C(O)NR^6R^7$, —O—($C_0$-$C_{10}$ alkylene)-$C(O)NR^6NR^7C(O)OR^6$, —O—($C_1$-$C_{10}$ alkylene)-C(O)(aryl)-N—N=$N^-$, —OC(O)—($C_1$-$C_{10}$ alkylene)-$C(O)OR^6$, —($C_0$-$C_{10}$ alkylene)-$C(O)NR^6R^7$, —($C_0$-$C_{10}$ alkylene)-$OC(O)NR^6R^7$, —$NO_2$, —($C_0$-$C_{10}$ alkylene)-$NR^6R^7$, —O—($C_2$-$C_{10}$ alkylene)-$NR^6R^7$, —$NR^6C(O)R^7$, —$NR^6C(O)OR^9$, —$NR^6C(O)NR^7R^8$, —$NR^6S(O)_{0-2}R^9$, —$N(S(O)_{0-2}R^9)_2$, —$CHNOR^6$, —$C(O)NR^6R^7$, —$C(O)NR^6NR^6R^7$, —$S(O)_{0-2}NR^6R^7$, —$S(O)_{0-2}R^9$, —O—C(O)—($C_1$-$C_{10}$ alkylene)-$C(O)NR^6R^7$, —OC(O)—($C_1$-$C_{10}$ alkylene)-$NR^6C(O)O$-(alkylaryl), —$P(O)(OR^{10})_2$, —($C_1$-$C_{10}$ alkylene)-$OSi(alkyl)_3$, —$CF_3$, —$OCF_3$, halo, alkoxyalkoxy, alkoxyalkoxyalkoxy, alkoxycarbonylalkoxy, alkoxyarylalkoxy, alkoxyiminoalkyl, alkyldioyl, allyl, allyloxy, aryloxycarbonyl, aryl, arylalkyl, aryloxy, arylalkoxy, aroyl, aroyloxy, arylsulfonyl, aroylaroyloxy, aroyl, arylalkoxycarbonyl, benzoylbenzoyloxy, carboxy, cyano, cycloalkyl, cycloalkylalkyl, cycloalkenyl, cycloalkenylalkyl, heteroaryl, heteroarylalkenyl, heteroarylalkynyl, heteroarylalkyl, heteroarylalkoxy, heteroarylsulfonyl, heteroarylthio, dioxolanyl, heterocyclyl, heterocyclylalkyl, heterocyclylcarbonyl, heterocyclylcarbonylalkoxy, hydroxy, hydroxyalkyl, alkylsulfonyl, and ring substituents comprising a moiety replacing one available hydrogen atom on a ring system or simultaneously replacing two available hydrogens on adjacent carbon atoms on a ring system as defined below;

$Q^5$ is 1 to 5 substituents independently selected from the group consisting of acyl, alkyl, alkylaryl, alkylheteroaryl, alkylsulfonyl alkenyl, alkoxy, alkoxycarbonyl, alkynyl, —($C_0$-$C_{30}$ alkylene)-G, —($C_0$-$C_{10}$ alkylene)-$OR^6$, —($C_0$-$C_{10}$ alkylene)-$C(O)R^6$, —($C_0$-$C_{10}$ alkylene)-$C(O)OR^6$, —($C_0$-$C_{10}$ alkylene)-$OC(O)R^6$, —($C_0$-$C_{10}$ alkylene)-$OC(O)OR^9$, —CH=CH—$C(O)R^6$—CH=CH—$C(O)OR^6$, —C≡C—$C(O)OR^6$, —C≡C—$C(O)R^6$, —O—($C_1$-$C_{10}$ alkylene)-$OR^6$, —O—($C_1$-$C_{10}$ alkylene)-$C(O)R^6$, —O—($C_1$-$C_{10}$ alkylene)-$C(O)OR^6$, —CN, —C(=N—CN)—$NH_2$, —C(=NH)—$NHR^{10}$, —O—($C_1$-$C_{10}$ alkylene)-$C(O)NR^6R^7$, —O—($C_0$-$C_{10}$ alkylene)-$C(O)NR^6NR^7C(O)OR^6$, —O—($C_1$-$C_{10}$ alkylene)-C(O)(aryl)-N—N=$N^-$, —OC(O)—($C_1$-$C_{10}$ alkylene)-$C(O)OR^6$, —($C_0$-$C_{10}$ alkylene)-$C(O)NR^6R^7$, —($C_0$-$C_{10}$ alkylene)-$OC(O)NR^6R^7$, —$NO_2$, —($C_0$-$C_{10}$ alkylene)-$NR^6R^7$, —O—($C_2$-$C_{10}$ alkylene)-$NR^6R^7$, —$NR^6C(O)R^7$, —$NR^6C(O)OR^9$, —$NR^6C(O)NR^7R^8$, —$NR^6S(O)_{0-2}R^9$, —$N(S(O)_{0-2}R^9)_2$, —$CHNOR^6$, —$C(O)NR^6R^7$, —$C(O)NR^6NR^6R^7$, —$S(O)_{0-2}NR^6R^7$, —$S(O)_{0-2}R^9$, —O—C(O)—($C_1$-$C_{10}$ alkylene)-$C(O)NR^6R^7$, —OC(O)—($C_1$-$C_{10}$ alkylene)-$NR^6C(O)O$-(alkylaryl), —$P(O)(OR^{10})_2$, —($C_1$-$C_{10}$ alkylene)-$OSi(alkyl)_3$, —$CF_3$, —$OCF_3$, halo, alkoxyalkoxy, alkoxyalkoxyalkoxy, alkoxycarbonylalkoxy, alkoxyarylalkoxy, alkoxyiminoalkyl, alkyldioyl, ally, allyloxy, aryloxycarbonyl, aryl, arylalkyl, aryloxy, arylalkoxy, aroyl, aroyloxy, arylsulfonyl, aroylaroyloxy, aroyl, arylalkoxycarbonyl, benzoylbenzoyloxy, carboxy, cyano, cycloalkyl, cycloalkylalkyl, cycloalkenyl, cycloalkenylalkyl, heteroaryl, heteroarylalkenyl, heteroarylalkynyl, heteroarylalkyl, heteroarylalkoxy, heteroarylsulfonyl, heteroarylthio, dioxolanyl, heterocyclyl, heterocyclylalkyl, heterocyclylcarbonyl, heterocyclylcarbonylalkoxy, hydroxy, hydroxyalkyl, alkylsulfonyl, and ring substituents comprising a moiety replacing one available hydrogen atom on a ring system or simultaneously replacing two available hydrogens on adjacent carbon atoms on a ring system as defined below;

wherein optionally one or more carbon atoms of the —($C_0$-$C_{30}$ alkylene)-radical of $Q^1$, $Q^2$, $Q^3$, $Q^4$ and $Q^5$ is independently replaced by —O—, —C(O)—, —CH═CH—, —C≡C—, —N(alkyl)-, —N(alkylaryl)- or —NH—;

G is selected from the group consisting of a sugar residue, disugar residue, trisugar residue, tetrasugar residue, sugar acid, amino sugar, amino acid residue, oligopeptide residue comprising 2 to 9 amino acids, trialkylammoniumalkyl radical and —S(O)$_2$—OH, $R^2$ and $R^3$ can be the same or different and each is independently selected from the group consisting of hydrogen, alkyl and aryl;

$R^6$, $R^7$ and $R^8$ can be the same or different and each is independently selected from the group consisting of hydrogen, alkyl, aryl, arylalkyl, cycloalkyl, and a protecting group; and each $R^9$ is independently alkyl, cycloalkyl, aryl or arylalkyl.

each $R^{10}$ is independently H or alkyl;

q is 0 or 1;

r is 0 or 1;

m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5.

As used above, and throughout the specification, the following terms, unless otherwise indicated, shall be understood to have the following meanings:

The statements above, wherein, for example, $Q^1$ and $Q^2$ are said to be independently selected from a group of substituents, means that $Q^1$ and $Q^2$ are independently selected, but also that where an $Q^1$ or $Q^2$ variable occurs more than once in a molecule, those occurrences are independently selected (e.g., if $Q^1$ is —$OR^6$ wherein $R^6$ is hydrogen, $Q^2$ can be —$OR^6$ wherein $R^6$ is alkyl). Those skilled in the art will recognize that the size and nature of the substituent(s) will affect the number of substituents that can be present.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

As used herein, the term "acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

As used herein, the term "alkyl" means an aliphatic hydrocarbon group that can be straight or branched and comprises 1 to about 20 carbon atoms in the chain. Preferred alkyl groups comprise 1 to about 12 carbon atoms in the chain. More preferred alkyl groups comprise 1 to about 6 carbon atoms in the chain. "Branched" means that one or more lower alkyl groups such as methyl, ethyl or propyl, are attached to a linear alkyl chain. The alkyl group can be substituted by one or more substituents independently selected from the group consisting of halo, aryl, cycloalkyl, cyano, hydroxy, alkoxy, alkylthio, amino, —NH(alkyl), —NH(cycloalkyl), N(alkyl)$_2$ (which alkyls can be the same or different), carboxy and —C(O)O-alkyl, Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylaryl" means an alkyl-aryl-group in which the alkyl and aryl are as described herein. Preferred alkylaryls comprise a lower alkyl group. Non-limiting example of a suitable alkylaryl group is tolyl. The bond to the parent moiety is through the aryl. "Alkylheteroaryl" means an alkylaryl moiety in which the aryl group comprises a heteroaryl group as defined herein.

"Alkylsulfonyl" means an alkyl-S(O$_2$)— group. Preferred groups are those in which the alkyl group is lower alkyl. The bond to the parent moiety is through the sulfonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano, heteroaryl, and alkoxy. When substituted the alkenyl group is described sometime herein for convenience by appending the substituent name, for example, when substituted with a heteroaryl group it can be described as a "heteroarylalkenyl" group. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkoxy" means an alkyl-O— group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen. Used successively, for example, alkoxyalkoxy, means an alkoxy moiety which is itself substituted with one or more alkoxy moieties.

"Alkoxyarylalkoxy" means an alkyl-O-aryl-alkylene-O— group in which the alkyl, alkylene and aryl groups are as previously described. Useful alkoxyarylalkoxy groups can comprise 7 to about 26 carbon atoms, preferably 7 to about 12 carbon atoms. A non-limiting example of a suitable alkoxyarylalkoxy group is methoxybenzyloxy. The alkoxyarylalkoxy is linked to an adjacent moiety through the ether oxygen.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl "Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl. For convenience the term "arylalkoxycarbonyl" is sometimes used alternatively herein.

"Alkoxycarbonylalkoxy" means an alkyl-O—C(O)-alkylene-O— group in which the alkyl and alkylene groups are as previously described. Useful alkoxycarbonylalkoxy groups can comprise 3 to about 12 carbon atoms, preferably 3 to about 8 carbon atoms. A non-limiting example of a suitable alkoxycarbonylalkoxy group is $CH_3CH_2$—O—C(O)—$CH_2$—O—. The alkoxycarbonylalkoxy is linked to an adjacent moiety through the ether oxygen.

"Alkoxyiminoalkyl" means an alkyl-O—N=CH-alkylene-group in which the alkyl and alkylene groups are as previously described. Useful alkoxyiminoalkyl groups can comprise 2 to about 12 carbon atoms, preferably 2 to about 8 carbon atoms. The alkoxyiminoalkyl is linked to an adjacent moiety through the alkylene group.

"Alkyldioyl" means an ROC(O)-alkylene-C(O)—O— group in which R is alkyl or H and the alkylene group is as previously described. Useful alkyldioyl groups can comprise 2 to about 12 carbon atoms, preferably 2 to about 8 carbon atoms. Non-limiting examples of suitable alkyldioyl groups include 1,3-propanediol. The alkyldioyl is linked to an adjacent moiety through the ester oxygen.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of halo, alkyl, aryl, cycloalkyl, cyano, heteroaryl, and alkoxy. When substituted the alkynyl group is described sometime herein for convenience by appending the substituent name, for example, when substituted with a heteroaryl group it can be described as a "heteroarylalkynyl" group.

"Allyl" means $(R^2R^3)C=CR^2—C(R^2R^3)$—, wherein $R^2$ and $R^3$ can be the same or different and are selected independently for each occurrence from the group consisting of hydrogen, alkyl and aryl;

"Allyloxy" means $H_2C=CH$—O—. The allyloxy is linked to an adjacent moiety through the ether oxygen.

"Aryl" means an aromatic monocyclic or mufticyclic ring system comprising about 5 to about 14 carbon atoms, preferably about 6 to about 10 carbon atoms. The aryl group can be substituted with one or more "ring system substituents" which may be the same or different, and are as defined herein. Non-limiting examples of suitable aryl groups include phenyl, naphthyl, indenyl, tetrahydronaphthyl and indanyl. "Arylene" means a bivalent phenyl group, including ortho, meta and para-substitution.

"Aralkyl" or "arylalkyl" means an aryl-alkylene-group in which the aryl and alkylene are as previously described. Preferred aralkyls comprise a lower alkyl group. Non-limiting examples of suitable aralkyl groups include benzyl, phenethyl and naphthlenylmethyl. The aralkyl is linked to an adjacent moiety through the alkylene group.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkoxy" or "arylalkyloxy" means an aralkyl-O— group in which the aralkyl group is as previously described. Non-limiting examples of suitable aralkoxy groups include benzyloxy and 1- or 2-naphthalenemethoxy. The bond to the parent moiety is through the ether oxygen. "Aralkoxycarbonyl" means an aralkoxy-C(O)— group in which the aralkoxy group is as previously described.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Aroyloxy" means an aroyl-O— group in which the aroyl group is as previously described. The bond to the parent moiety is through the ether oxygen. Non-limiting examples of suitable groups include benzoyloxy and 1- and 2-naphthoyloxy.

"Carboxy" means R"-C(O)O—, wherein R" is an aliphatic or aromatic hydrocarbon radical which may or may not be substituted.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be substituted with one or more "ring system substituents" which may be the same or different, and are as defined below. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalinyl, norbornyl, adamantyl and the like. "Cycloalkylene" refers to a corresponding bivalent ring, wherein the points of attachment to other groups include all positional isomers.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Dioxolanyl" means.

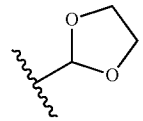

"Halo" refers to fluorine, chlorine, bromine or iodine radicals. Preferred are fluoro, chloro or bromo, and more preferred are fluoro and chloro.

"Heteroaryl" means a monocyclic or multicyclic aromatic ring system of about 5 to about 14 ring atoms, preferably about 5 to about 10 ring atoms, in which one or more of the atoms in the ring system is/are atoms other than carbon, for example nitrogen, oxygen or sulfur. The heteroatom(s) interrupt a carbocyclic ring structure and have a sufficient number of delocalized pi electrons to provide aromatic character, provided that the rings do not contain adjacent oxygen and/or sulfur atoms. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be oxidized to form the corresponding N-oxide. All regioisomers are contemplated, e.g., 2-pyridyl, 3-pyridyl and 4-pyridyl. Examples of useful 6-membered heteroaryl groups include pyridyl, pyrimidinyl, pyrazinyl, pyridazinyl and the like and the N-oxides thereof. Examples of useful 5-membered heteroaryl rings include furyl, thienyl, pyrrolyl, thiazolyl, isothiazolyl, imidazolyl, pyrazolyl and isoxazolyl. Useful bicyclic groups are benzo-fused ring systems derived from the heteroaryl groups named above, e.g., quinolyl, phthalazinyl, quinazolinyl, benzofuranyl, benzothienyl and indolyl.

"Heteroarylalkyl" or "heteroaralkyl" means a heteroaryl-alkylene-group in which the heteroaryl and alkyl are as previously described. Preferred heteroaralkyls contain a lower alkyl group. Non-limiting examples of suitable heteroaralkyl groups include pyridylmethyl, 2-(furan-3-yl)ethyl and quinolin-3-ylmethyl. The bond to the parent moiety is through the alkylene. In the same manner, "heteroarylalkenyl" and "heteroarylalkynyl" mean a heteroaryl group, as defined herein, bonded to the parent moiety through, respectively, an alkenyl and an alkenynyl group. "Heteroarylalkoxy" means a heteroaryl-alkylene-O— group in which the heteroaryl and alkylene are as previously described.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclylalkyl" means a heterocyclyl-alkylene-group in which the heterocyclyl and alkylene groups are as previously described. Preferred heterocyclylalkyls contain a lower alkylene group. The bond to the parent moiety is through the alkylene. "Heterocyclylcarbonyl" means a heterocyclyl-C(O)— group in which the heterocyclyl is as previously described.

Preferred heterocyclylcarbonyls contain a lower alkyl group. The bond to the parent moiety is through the carbonyl. "Heterocyclylcarbonylalkoxy" means a heterocyclyl-C(O)-alkoxy-group in which the heterocyclyl and alkoxy are as previously described.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, aralkenyl, heteroaralkyl, heteroarylalkynyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—Y$_1$Y$_2$NSO$_2$— and —SONY$_1$Y$_2$, wherein Y$_1$ and Y$_2$ may be the same or different and are independently selected from the group consisting of hydrogen, alkyl, aryl, and cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

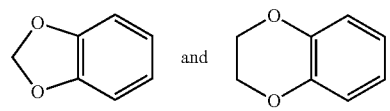 [SMILES: c1ccc2c(c1)OCO2 ; c1ccc2c(c1)OCCO2]

"Sugar residue" means a moiety derived from an aldose or ketose that has 3 to 7 carbon atoms and may belong to the D or L series. Non-limiting examples of suitable aldoses from which the sugar residue can be formed include glucose, mannose, galactose, ribose, erythrose and glyceraldehydes. A non-limiting example of a suitable ketose from which the sugar residue can be formed is fructose.

"Disugar residue" means a moiety derived from a sugar that can be hydrolyzed to two monosaccharide molecules. Non-limiting examples of suitable compounds from which the disugar residue can be formed include maltose, lactose, cellobiose and sucrose.

Examples of sugar residues and disugar residues include those moieties G listed in detail above.

Di-, tri- or tetrasaccharides are formed by acetal-like binding of two or more sugars. The bonds may be in α or β form. "Trisugar residue" means a moiety derived from a sugar that can be hydrolyzed to three monosaccharide molecules. "Tetrasugar residue" means a moiety derived from a sugar that can be hydrolyzed to four monosaccharide molecules.

If the sugar is substituted, the substitution is preferably at the hydrogen atom of an OH group of the sugar.

"Sugar acid" means an sugar residue, such as can be formed from glucuronic acid, galacturonic acid, gluconic acid, galactonic acid, mannonic acid, glucaric acid and galactaric acid.

"Amino sugar" means an amino-substituted sugar residue such as can be formed from glucosamine, galactosamine, glucamine or 3-amino-1,2-propanediol.

Suitable protective groups for the hydroxyl groups of the sugars include benzyl, acetyl, benzoyl, pivaloyl, trityl, tert-butyldimethylsilyl, benzilidene, cyclohexidene or isopropylidene protective groups.

"Amino acid residue" means a moiety derived from an amino acid. The amino acid moiety can be prepared from the D or L forms of the amino acid. Non-limiting examples of suitable amino acids from which the amino acid residue can be prepared include alanine, arginine, asparagine, aspartic acid, cysteine, cystine, glutamic acid, glutamine, glycine, histidine, hydroxylysine, hydroxyproline, isoleucine, leucine, lysine, methionine, phenylanine, proline, serine, threonine, tryptophane, tyrosine, valine, 2-aminoadipic acid, 3-aminoadipic acid, beta-alanine, 2-aminobutyric acid, 4-aminobutyric acid, piperidino carboxylic acid, 6-aminocaproic acid, 2-aminoheptanoic acid, 2-(2-thienyl)glycine, penicillamine, N-ethylasparagine, 2-aminoisobutyric acid, 2-aminoisobutyric acid, 2-aminopimelic acid, 2,4-diaminobutyric acid, desmosine, 2,2-diaminopimelic acid, 2,3-diaminopropioninc acid, N-ethylglycine, 3-(2-thienylalanine, sarcosine, N-methylisoleucine, 6-N-methyllysine, N-methylvaline, norvaline, norleucine, ornithine and N-methylglycine.

"Oligopeptide residue" means the residue of a peptide constructed of 2 to 9 of the amino acids mentioned above.

"Trialkylammonium alkyl radical" means the group

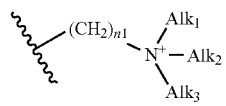

wherein n1 is 0 to 10 and $Alk_1$, $Alk_2$ and $Alk_3$ can be the same or different and each is a straight or branched alkyl radical having 1 to 20 carbon atoms.

Azetidinone or β-lactam compounds prepared in accordance with the methods of the invention have at least one asymmetrical carbon atom. Accordingly, the methods of the invention are useful in the preparation of all isomers, including enantiomers, stereoisomers, rotamers, tautomers and racemates of the compounds of Formula (I) (where they exist) and are contemplated as being within the scope of products formed by the process of this invention. Accordingly, the invention includes the preparation of d and l isomers in both pure form and in admixture, including racemic mixtures. Utilizing the methods of the invention, isomers can be prepared using conventional techniques, either by reacting optically pure or optically enriched starting materials or by separating isomers of a compound of the Formula (I). As the term is used herein, isomers may also include geometric isomers, e.g., when a double bond is present. Preparation of polymorphous forms of the compounds of Formula (I), whether crystalline or amorphous, also are contemplated as being part of this invention.

Azetidinone or β-lactam compounds prepared in accordance with the methods of the invention having an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain azetidinone or β-lactam compounds prepared in accordance with the methods of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Accordingly, the methods of the invention are useful in the provision of salts formed with pharmaceutically acceptable amines such as ammonia, alkyl amines, hydroxyalkylamines, N-methylglucamine and the like.

Azetidinone or β-lactam compounds prepared in accordance with the methods of the invention having a carboxylic acid group can form pharmaceutically acceptable esters with an alcohol. Examples of suitable alcohols include methanol and ethanol. The methods of the present invention are also useful in the provision of such compounds.

Non-limiting examples of azetidinones that can be prepared using the processes of the present invention are disclosed in U.S. Pat. Nos. RE 37,721, 5,624,920, 5,656,624, 5,627,176, 5,633,246, 5,661,145, 5,688,785, 5,688,787, 5,688,990, 5,744,467, 5,756,470, 5,767,115, 5,846,966, each incorporated by reference herein.

Preferably, the processes of the present invention can be used to prepare the azetidinone (ezetimibe) represented by the structural formula (IV):

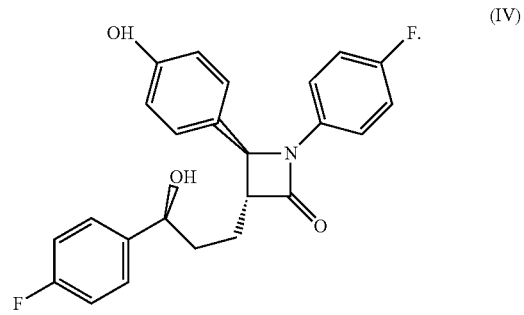 [SMILES: O=C1[C@H](CC[C@H](O)c2ccc(F)cc2)[C@@H](c2ccc(O)cc2)N1c1ccc(F)cc1]

Ezetimibe is commercially available in the US in ZETIA™ formulation and in combination with simvastatin in VYTORIN™ formulation from MSP Pharmaceuticals, Inc.

In one embodiment, the present invention provides a process for preparing an azetidinone, comprising reacting: (1) a β-(substituted-amino)amide, a β-(substituted-amino)-acid ester, or a β-(substituted-amino)thiolcarbonic acid ester with (2) at least one silylating agent and (3) at least one cyclizing agent described in detail below.

As used herein, the terms β-(substituted-amino)amide, β-(substituted-amino)acid ester, and β-(substituted-amino) thiolcarbonic acid ester refer to β-aminoamides, β-aminoacid esters, and β-aminothiol-carbonic acid esters refer to secondary amines, that is, compounds wherein the nitrogen is joined to the β-carbon, to a hydrogen molecule, and to a non-hydrogen substituent.

Starting β-(substituted-amino)amides, β-(substituted-amino)acid esters and β-(substituted-amino)thiolcarbonic acid esters are known or can be prepared by one skilled in the art using known methods. For example, suitable methods for preparing β-aminoamide compounds of Formula II are disclosed in WO 93/02048, incorporated by reference herein.

Those skilled in the art will recognize that for cyclization to proceed as desired, —$NH_2$, —SH and —OH substituents present on the β-(substituted-amino)amide, a β-(substituted-amino)acid ester, or a β-(substituted-amino)thiolcarbonic acid ester starting material must be converted to groups which will not be silylated, either preferentially or in addition to silylation of the substituted-amino portion of the molecule. Suitable protecting groups well known in the art include for —NH$_2$: t-butyldimethylsilyl, benzyl, benzoyl and t-butoxycarbonyl; for —SH: triphenylmethyl; and for —OH: lower alkoxy, e.g., methoxy, benzyloxy and t-butyldimethylsilyl.

In one embodiment, the β-(substituted-amino)amide comprises a carbamoyl portion B—C(O)—, wherein B is a deprotonated chiral auxiliary selected from the group consisting of

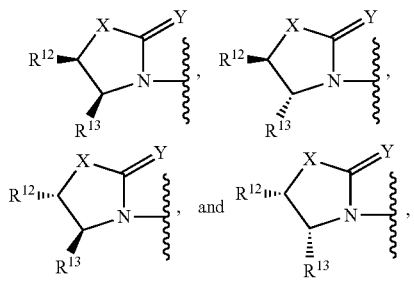

wherein X is —O—, —S— or —N(alkyl)-; Y is =O or =S; and $R^{12}$ and $R^{13}$ are each independently selected from the group consisting of alkyl, aryl and alkoxycarbonyl, or wherein one of $R^{12}$ or $R^{13}$ is as defined above and the other is hydrogen. Preferably, X and Y are each oxygen and $R^{12}$ is hydrogen and $R^{13}$ is phenyl, benzyl or isopropyl.

The aryl group of $R^{12}$ or $R^{13}$ can be independently selected from the group consisting of phenyl, naphthyl, benzyl, substituted phenyl, substituted naphthyl and substituted benzyl, wherein the substituents on the phenyl, naphthyl or benzyl are 1-3 substituents selected from the group consisting of alkyl, alkoxy, phenyl and benzyl.

In another embodiment, the β-(substituted-amino)amide comprises a carbamoyl portion B—C(O)—, where B is ($R^{14}$)($R^{15}$)N—, and $R^{14}$ and $R^{15}$ are each independently selected from the group consisting of alkyl, aryl, arylalkyl.

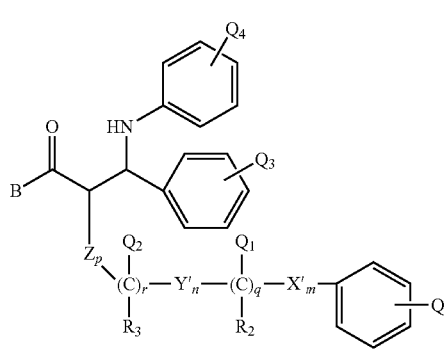

Preferably, the β-(substituted-amino)amide is represented by Formula (II):
wherein B, $R^2$, $R^3$, $R^6$, $R^7$, $R^8$, $R^9R^{10}$, $Q^1$, $Q^2$, $Q^3$, $Q^4$, $Q^5$, X', Y', Z, m, n, p, q, r are as defined above.

More preferably, $Q^4$ is selected from the group consisting of H, 3-fluoro-, and 4-fluoro- and $Q^5$ is selected from the group consisting of H, methyl-, 2-fluoro-, and 4-fluoro-.

Most preferably, the β-(substituted-amino)amide is represented by Formula (III):

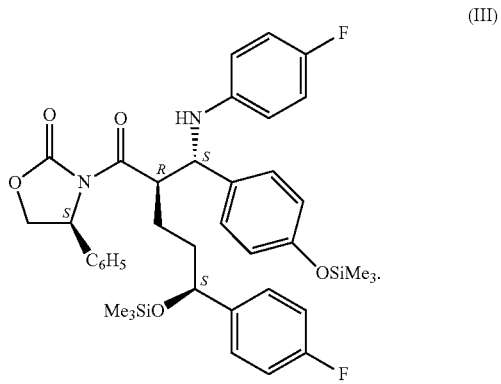

In another embodiment of the process of the present invention, a β-(substituted-amino)acid ester can be used as a reactant. Preferably, the β-(substituted-amino)acid ester comprises a carboxylic acid ester portion $R^{14}$—O—C(O)—, wherein $R^{14}$ is alkyl or aryl.

In another embodiment of the process of the present invention, a β-(substituted-amino)thiolcarbonic acid ester can be used as a reactant. Preferably, the β-(substituted-amino)thiolcarbonic acid ester comprises a thiolcarbonic acid ester portion $R^{14}$—S—C(O)—, wherein $R^{14}$ is alkyl or aryl.

As discussed above, the process comprises reacting (1) the β-(substituted-amino)amide, a β-(substituted-amino)-acid ester, or a β-(substituted-amino)thiolcarbonic acid ester with (2) one or more silylating agents and (3) one or more cyclizing agents described below.

Preferably the silylating agent is a silylenol ether. Non-limiting examples of suitable silylenol ethers include bistrimethylsilylacetamide, N-methyl-O-trimethyl silylacetamide or isopropenyloxy trimethylsilane. The silylating agent can be added in up to a stoichiometric amount or excess.

In the process of the present invention, suitable cyclizing agent(s) are: (a) selected from the group consisting of alkali metal carboxylates, quaternary ammonium carboxylates, quaternary ammonium hydroxides, quaternary ammonium alkoxides, quaternary ammonium aryloxides and hydrates thereof, or (b) the reaction product of:
  (i) at least one quaternary ammonium halide and at least one alkali metal carboxylate; or
  (ii) at least one quaternary ammonium chloride, quaternary ammonium bromide, or quaternary ammonium iodide and at least one alkali metal fluoride,
  wherein a quaternary ammonium moiety of the cyclizing agent is unsubstituted (i.e., quaternary ammonium) or substituted by one to four groups independently selected from the group consisting of alkyl, arylalkyl and arylalkyl-alkyl.

Non-limiting examples of suitable quaternary ammonium moieties include alkylammonium groups containing alkyl groups of 1-6 carbon atoms, e.g., tetra n-butylammonium. Examples of suitable arylalkyl-so groups include benzyltriethyl-ammonium and benzyl-trimethylammonium and examples of aryl-alkyl-ammonium include phenyltriethylammonium and phenyltrimethyl-ammonium.

The alkali metal carboxylate can be a carboxylate salt of an alkali metal selected from the group consisting of lithium, sodium, potassium and cesium, preferably potassium.

In one embodiment, the alkali metal carboxylate or quaternary ammonium carboxylate can comprise a carboxylate moiety selected from the group consisting of formate, acetate, propionate, butyrate, valerate, caproate, caprylate, laurate, myristate, palmitate, stearate, oleate, linoleate, linolenate, cyclohexanecarboxylate, phenylacetate, benzoate and toluate, preferably acetate.

In another preferred embodiment, the quaternary ammonium carboxylate is tetra n-butylammonium acetate. In another preferred embodiment, the silylating agent is bistrimethylsilylacetamide and the cyclizing agent is tetra n-butylammonium acetate.

In yet another preferred embodiment, the quaternary ammonium hydroxide is tetra n-butylammonium hydroxide.

As discussed above, the cyclizing agent can be the reaction product of (i) at least one quaternary ammonium halide and at least one alkali metal carboxylate in a catalytic to stoichiometric excess amount. Suitable quaternary ammonium moieties are discussed above. The quaternary ammonium halide can comprise a halide moiety selected from the group consisting of fluoride, chloride, bromide and iodide, preferably fluoride. In a preferred embodiment, the alkali metal carboxylate is potassium acetate.

In another embodiment, the cyclizing agent can be the reaction product of (ii) at least one quaternary ammonium chloride, quaternary ammonium bromide, or quaternary ammonium iodide and at least one alkali metal fluoride in a catalytic to stoichiometric excess amount. In a preferred embodiment, the cyclizing agent is the reaction product of tetra n-butylammonium bromide and potassium acetate. In another preferred embodiment, the cyclizing agent is the reaction product of tetra n-butylammonium bromide and cesium fluoride.

The reaction product (3)(b) can be formed in situ in the presence of reactants (1) and (2) or formed prior to reaction with reactants (1) and (2). Advantages of forming the reaction product (3)(b) in situ include that the anhydrous reactants are easier to handle and it may be less expensive to prepare the cyclizing agent from the reactants.

When a hydrated quaternary ammonium cyclizing agent is used, the reagent is added in a catalytic amount, i.e., about 1 to about 20 mole percent, preferably about 5 mole percent, and when an anhydrous quaternary ammonium cyclizing agent is used, it can be added in a catalytic up to a stoichiometric amount. When an alkali metal carboxylate is used, it is added in catalytic amount up to a stoichiometric amount compared to the starting β-amino compound. If added to the reaction mixture after the silylation agent, the fluoride reagent is added directly to the reaction mixture resulting from silylation, and is reacted at about 0° C. to 110° C., preferably about 20° C. to 60° C., for about 0.5 to about 6 hours, preferably about 1 hour.

In an alternative embodiment, one or more fluoride ion catalyst cyclizing agents can be used in combination with the cyclizing agents described above. Non-limiting examples of suitable fluoride ion catalyst cyclizing agents include quaternary alkyl-, aryl-alkyl- or arylalkyl-alkylammonium fluoride salt or a hydrate thereof, or a mixture thereof, wherein alkyl-, aryl-alkyl- or arylalkyl-alkylammonium are as defined above, or is an alkali metal fluoride salt or a hydrate thereof, such as cesium fluoride or potassium fluoride. When a fluoride ion catalyst cyclizing agent is used, the agent is added in an amount sufficient to replace the cyclizing agent discussed above on a 1:1 molar basis as desired. If added to the reaction mixture after the silylation agent, the fluoride reagent is added directly to the reaction mixture resulting from silylation, and is reacted at about 0° C. to 110° C., preferably about 20° C. to 60° C., for about 0.5 to about 6 hours, preferably about 1 hour. When the silylation reagent, cyclization agent and the fluoride reagent are added simultaneously, the reaction is conducted under similar conditions.

The order of addition of the components of this process is not critical to the preparation of the azetidinone product. For example, the starting β-(substituted-amino)amide, β-(substituted-amino)acid ester, or β-(substituted-amino)thiolcarbonic acid ester can first be reacted with the silylating agent and then reacted with the cyclizing agent, or the starting compound can be added to a mixture of the silylating agent and the cyclizing agent.

Silylation is effected by reacting the starting material with a silyl-enol ether silylating agent such as bistrimethylsilyl acetamide (BSA), N-methyl-O-trimethylsilyl acetamide or iso-propenyloxy trimethylsilane, preferably BSA, in a suitable inert organic solvent at 0° C. to 110° C., preferably at about 20° C. to 90° C., and more preferably at ambient temperature (e.g., about 25° C.). The reaction is preferably carried out in a dry, inert atmosphere, e.g., the solvent is dried, typically with molecular sieves, and the reaction is carried out under nitrogen. When the silylation and cyclization are done sequentially, i.e., the silylating agent is reacted with the starting material first, the silylation reaction can be allowed to continue for up to about two hours, but preferably the cyclization step is carried out immediately after silylation, or the silylating agent and the cyclizing agent are added simultaneously.

Another aspect of the present invention is a process for preparing an azetidinone represented by the structural formula (I):

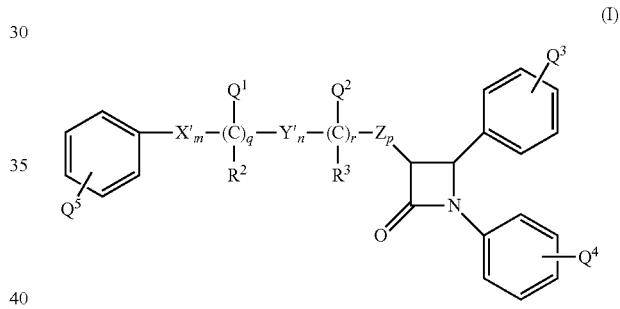

or pharmaceutically acceptable salts or solvates of the azetidinone of Formula (I), wherein in Formula (I) above: $R^2$, $R^3$, $R^6$, $R^7$, $R^8$, $R^9$, $R^{10}$, $Q^1$, $Q^2$, $Q^3$, $Q^4$, $Q^5$, X', Y', Z, m, n, p, q, r are as above, comprising the step of reacting:
(a) a compound of Formula (II):

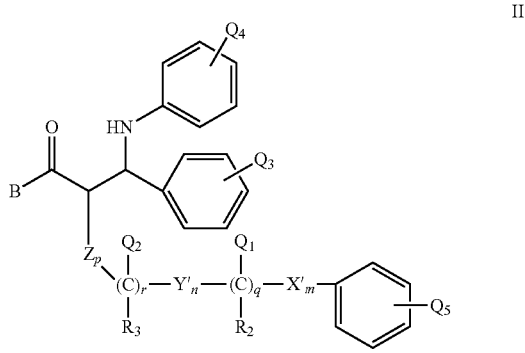

wherein $R_2$, $R_3$, $Q_1$, $Q_2$, $Q_3$, $Q_4$, $Q_5$, X', Y', Z, m, n, p, q, r are as above, and B is a deprotonated chiral auxiliary selected from the group consisting of

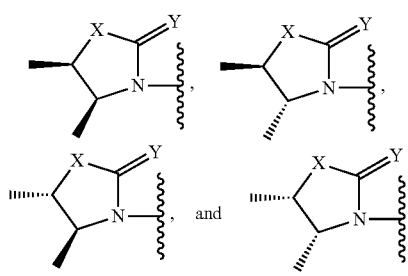

wherein X is —O—, —S— or —N($C_1$-$C_6$ alkyl)-; Y is =O or =S; and $R^{12}$ and $R^{13}$ are each independently selected from the group consisting of alkyl, aryl and alkoxycarbonyl, or wherein one of $R^{12}$ or $R^{13}$ is as defined above and the other is hydrogen, or B is ($R^{14}$)($R^{15}$)N—, wherein $R^{14}$ and $R^{15}$ are each independently selected from the group consisting of alkyl and aryl;

with (b) at least one silylating agent and (c) at least one cyclizing agent discussed above.

In a preferred embodiment, the process described above is used for preparing an azetidinone represented by the structural Formula (IV):

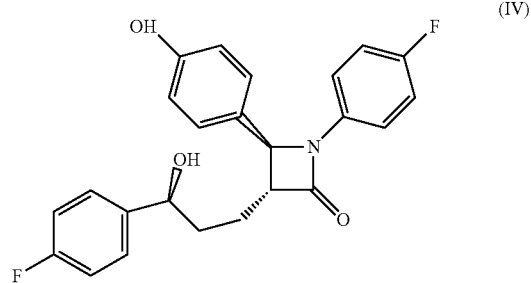 [SMILES: O=C1[C@H](CC[C@H](O)c2ccc(F)cc2)[C@@H](c2ccc(O)cc2)N1c1ccc(F)cc1]

comprising reacting a β-(substituted-amino)amide of Formula (III) above with (b) at least one silylating agent and (c) at least one cyclizing agent as described above.

Another aspect of the present invention is a process for preparing a compound represented by the structural Formula (IV) above, comprising:

(a) reacting p-fluorobenzoylbutyric acid of Formula V with pivaloyl chloride and acylating the product with a chiral auxiliary of Formula VI to obtain a ketone of Formula VII:

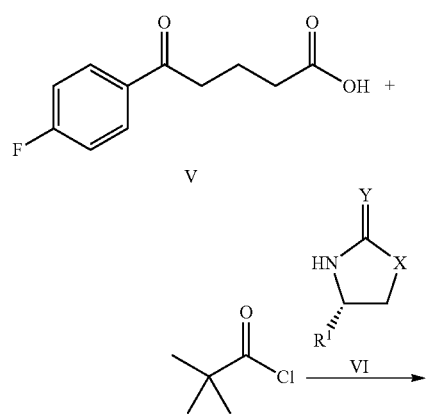

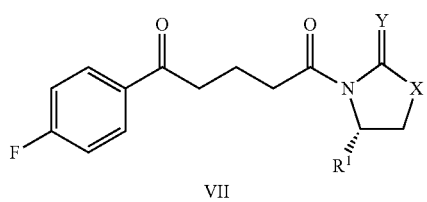

wherein X is —O—, —S— or —N($C_1$-$C_6$ alkyl); Y is =O or =S; and $R^1$ is alkyl, aryl or alkoxycarbonyl;

(b) reducing the ketone of Formula VII in the presence of a chiral catalyst to an alcohol of Formula VIII:

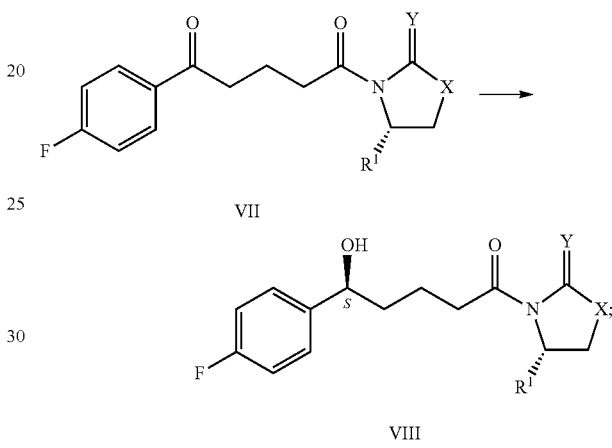

(c) reacting the chiral alcohol of Formula VIII, an imine of formula IX and a silyl protecting agent, then condensing the silyl-protected compounds to obtain a β-(substituted-amino) amide of Formula XII, wherein Prot is a silyl protecting group:

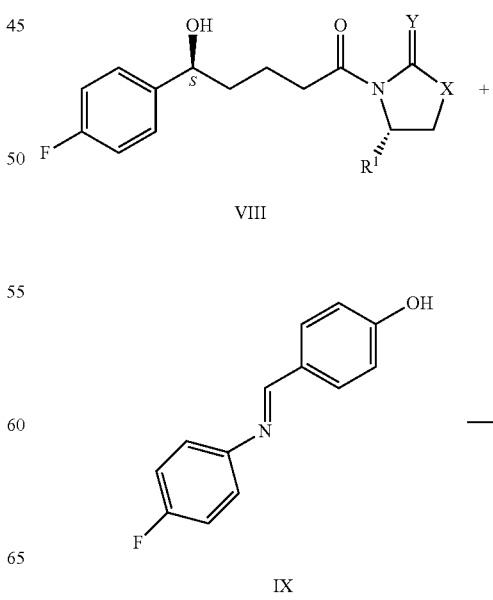

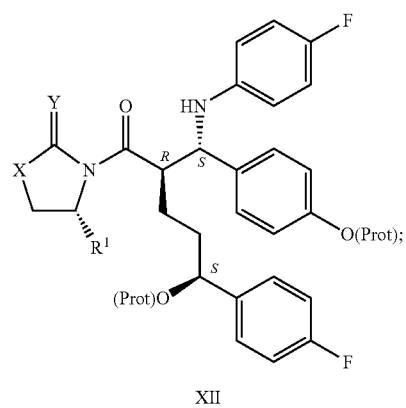

XII (d) cyclizing the β-(substituted-amino)amide of formula XII with a silylating agent and a cyclizing agent discussed above, to obtain the compound of Formula XI:

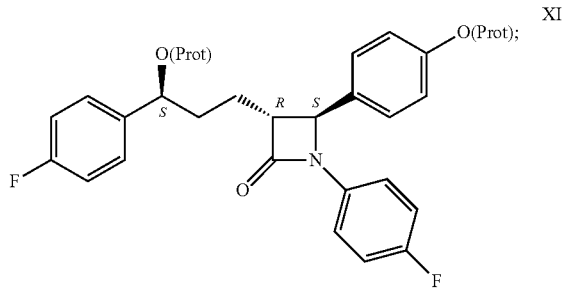

XI and (e) removing the silyl protecting groups.

In another embodiment, the present invention provides a process for preparing a compound represented by the Formula (IV) above, comprising:

reacting a chiral alcohol of Formula VIII, an imine of Formula IX and a silyl protecting agent, then condensing the silyl-protected compounds to obtain a β-(substituted-amino) amide of Formula XII, wherein X is —O—, —S— or —N($C_1$-$C_6$ alkyl); Y is =O or =S; and $R^1$ is alkyl, aryl or alkoxycarbonyl, and wherein Prot is a silyl protecting group:

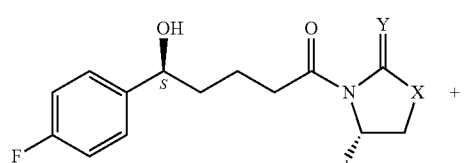

VIII

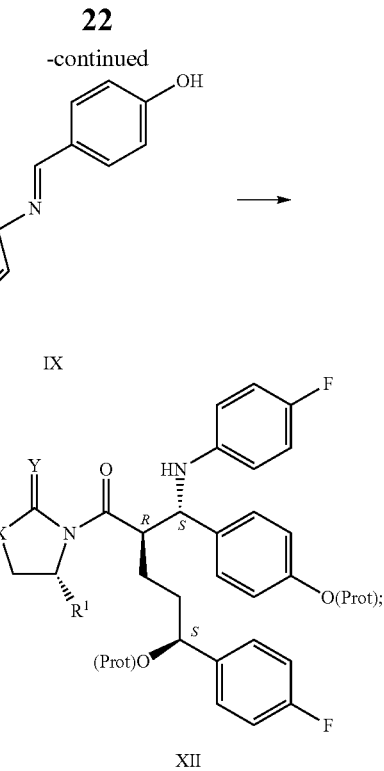

IX

XII cyclizing the β-(substituted-amino)amide of Formula XII with a silylating agent and a cyclizing agent discussed above, to obtain the compound of Formula XI:

XI and removing the silyl protecting groups.

Another aspect of the present invention is a process for preparing a compound represented by the Formula (IV):

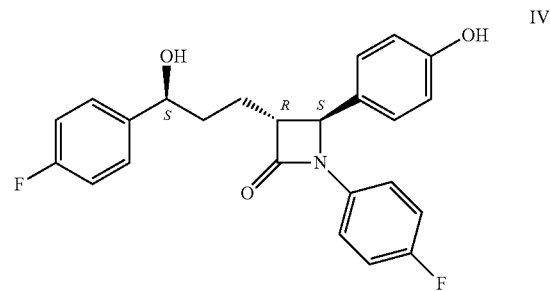

IV cyclizing the β-(substituted-amino)amide of formula XII
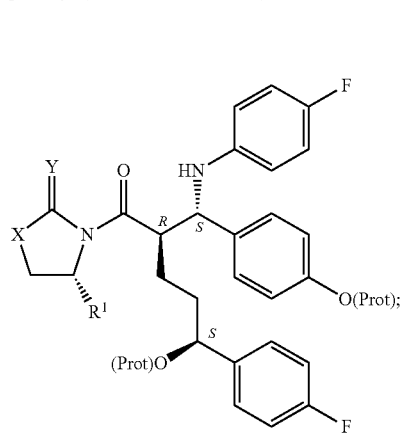
with a silylating agent and a cyclizing agent discussed above, to obtain the compound of Formula XI:
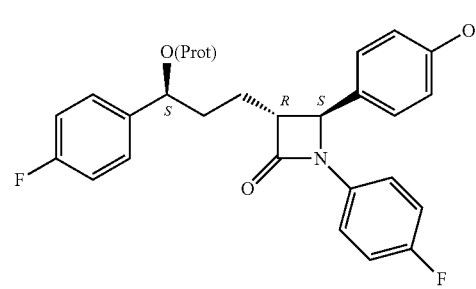
and
  removing the silyl protecting groups.
  Preferred reaction conditions are shown in the following scheme:
Step (a):
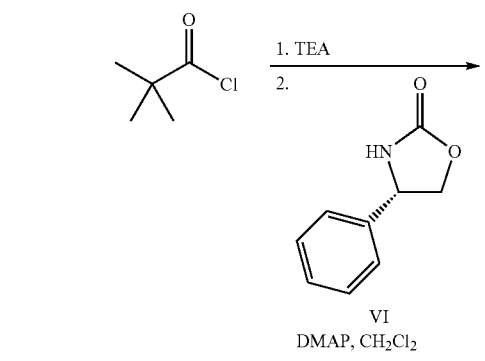
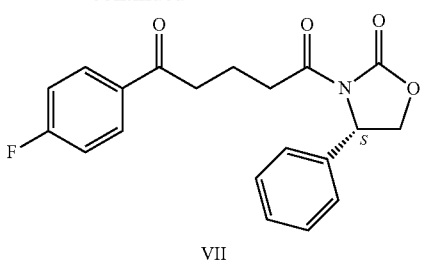
Step (b):
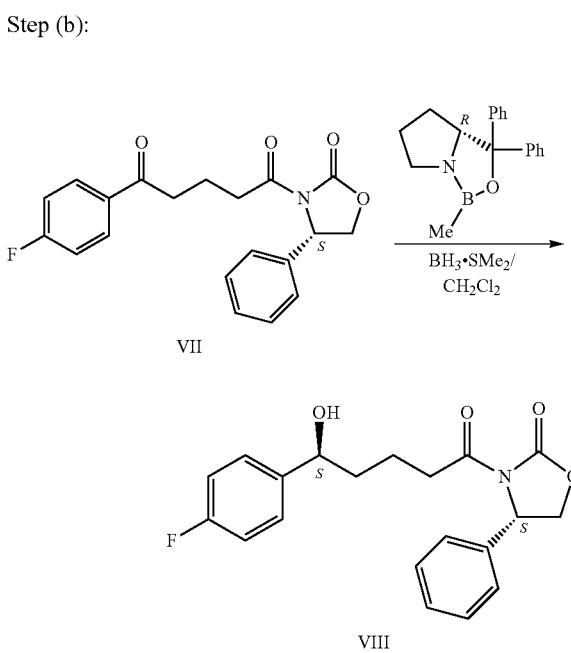
Step (c):
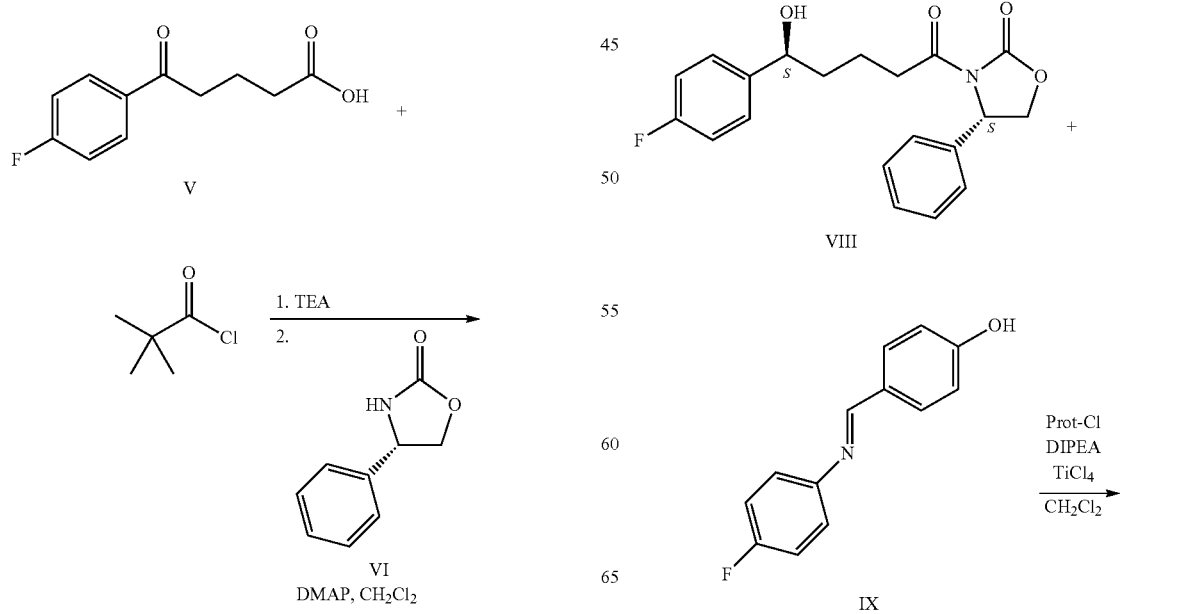
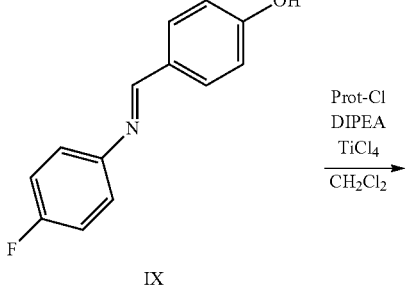

Step (d)

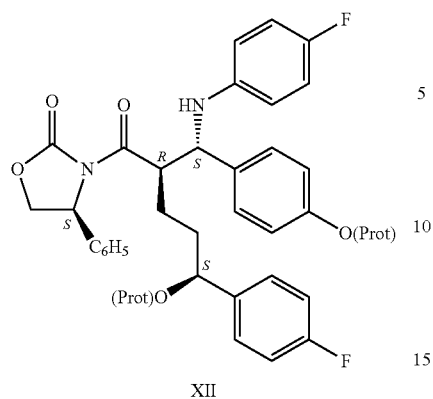

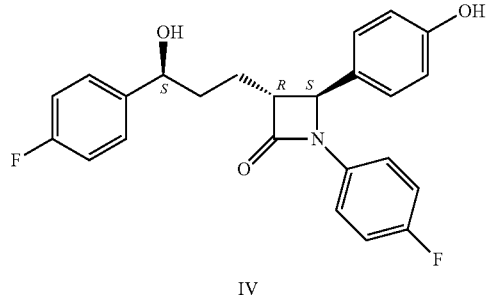

IV

In the reaction scheme above, TEA is triethylamine, DMAP is 4-dimethyl-amino pyridine, DIPEA is diisopropylethylamine, BSA is bistrimethylsilyl acetamide, TBAOAc is tetra n-butyl-ammonium acetate, t-BuOMe is t-butyl methyl ether and Prot is a silyl protecting group as defined above.

Starting materials of Formulae V and VI are known in the art, and the procedure of step (a) for reacting a compound of Formula V and a compound of Formula VI is known in the art. Preferably, the chiral auxiliary of Formula VI is exemplified by the formula:

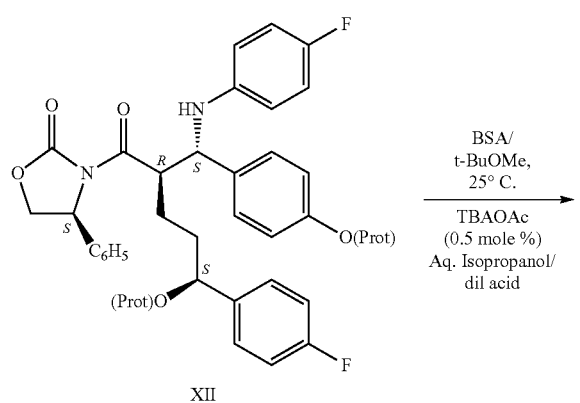

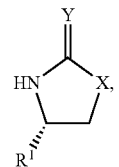

wherein Y is =O, X is —O— and $R^1$ is phenyl, benzyl or $C_1$-$C_6$ alkyl. A preferred chiral auxiliary is

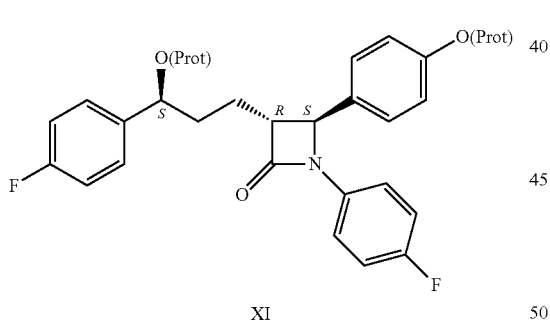

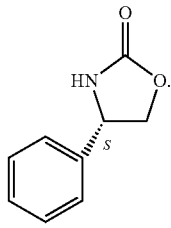

See the example below for typical reaction conditions.

Similarly, the procedure of step (b) for reducing a ketone to a hydroxy group using a borane reducing agent such as $BH_3 \cdot S(CH_3)_2$ in the presence of a chiral catalyst such as (R)-tetrahydro-1-methyl-3,3-diphenyl-1H,3H-pyrrolo(1,2-c)(1,3,2) oxaza-borolidine is known: See U.S. RE 37,721, U.S. Pat. No. 6,207,822 and U.S. Pat. No. 6,627,757, each incorporated by reference herein.

Step (e):

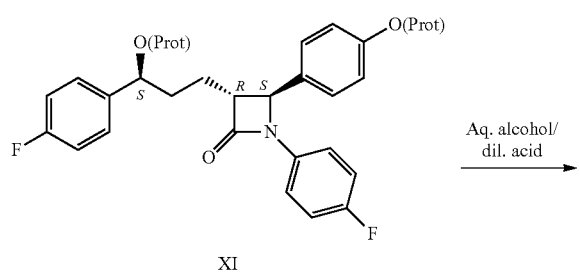

In step (c), the chiral alcohol, VIII, and the imine, IX, are protected with a suitable hydroxy-protecting group, preferably a silyl protecting group such as that derived from chlorotrimethylsilane (TMSCl) or t-butyldimethyl-silyl chloride (TBDMSCl). The alcohol (1 equivalent) and imine (preferably 1-3 equivalents) are added to an anhydrous solvent such as $CH_2Cl_2$, the reaction mixture is cooled to –10° to 15° C., a tertiary amine base such as DIPEA is added (preferably 2-4 equivalents), and sufficient silylating reagent to react with both the alcohol and the imine is added (e.g., 2-4 equivalents). After silylation is complete, the alcohol and imine are condensed by reacting at −20° to −35° C. with at least 1 equivalent of a Lewis acid such as $TiCl_4$, in the presence of a tertiary amine base (preferably 1-3 equivalents) such as DIPEA for 2-4 hours. The reaction is quenched, for example by treating with an acid such as glacial acetic acid followed by aqueous tartaric acid solution; the resultant product is extracted and crystallized using conventional procedures.

The azetidinone resulting from the processes of the present invention can be purified by appropriate standard procedures such as column chromatography or crystallization.

The term "suitable inert organic solvent" as used above means any organic solvent or combination of solvents that is unreactive in the reaction being conducted and is a solvent for the reactants. Typical suitable solvents are halogenated compounds such as dichloromethane; heterocyclic compounds such as tetrahydrofuran (THF); DMSO; dimethyl-formamide (DMF); acetonitrile; and carbocyclic aromatics such as toluene. Preferred are toluene, THF and dichloromethane.

The following examples illustrate the process of this invention. Although the examples are directed to C-3, C-4 disubstituted compounds and the stereochemistry of the reactants and intermediates are indicated in the various depicted structural formulas in the following examples, it is to be understood that the process of this invention is operative for azetidinones regardless of stereochemistry, and involves merely the selection of reactants having the desired racemic or stereochemical configuration and the selection of reaction conditions which result in the desired configuration in the product.

EXAMPLES

Starting materials useful in the processes of the present invention can be made by the following procedures:
Preparation of 4-(4-Fluorobenzoyl)Butyric Acid:

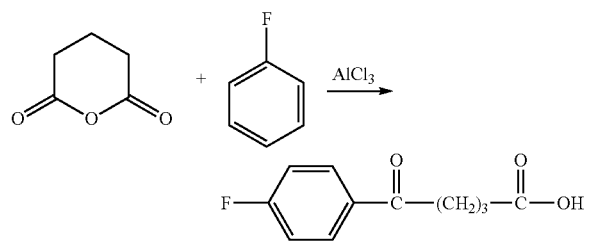

Charged 260 g of anhydrous $AlCl_3$ (1.87 moles) to a 2 L 3-neck round bottom flask, added 300 mL fluorobenzene (307.5 g; 3.2 moles) and cooled the mixture in an ice bath to 5° C. Added a hazy suspension of 100 g glutaric anhydride (0.86 mole) in 400 mL fluorobenzene (4.3 moles) through an addition funnel over a period of 45 min., and maintained the temperature below 12° C. The reaction mixture was warmed to ambient temperature gradually and agitated at r.t. for about 90 min.; checked for completion by NMR. Cooled the reaction mixture to 0 to 5° C., then added a cold aqueous solution (700 ml) of 1N HCl carefully to the mixture to destroy any unreacted $AlCl_3$, keeping the temperature of the mixture below 20° C. during the early part of the acid addition, and below 40° C. for the rest of the time. Poured the entire mixture into a 2 L 1:1 mixture of water and ice (v/w) to precipitate out crude products, filtered the white suspension and washed well with water. Added the white residue to 3 L of aqueous saturated solution (~5%) of $NaHCO_3$, heated the basic mixture on a steam bath for one hour and filtered the batch while hot through a thin pad of celite. Cooled the filtrate to r.t., added about 320 mL of concentrated HCl dropwise into the filtrate to pH 1 to crystallize out products, and agitated the white suspension in an ice bath for 30 min. Filtered the batch, washed the wet cake with ice cold water and dried in a vacuum oven at 50° C. for 16 h to obtain 143.2 g of 4-(4-fluorobenzoyl)-butyric acid; m.p. 141 to 142° C., isolated yield: 79.3%.

Preparation of Imine:

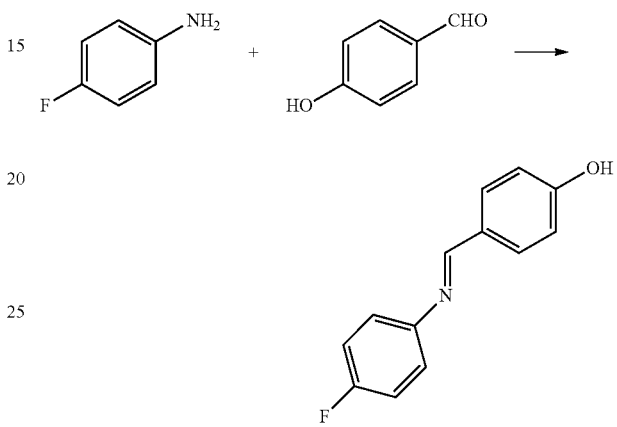

Equipped a three necked 1 L flask with a mechanical stirrer, thermometer and an addition funnel. Added 480 mL of isopropanol, 144 g (1.18 moles) of p-hydroxybenzaldehyde (endothermic) and agitated the mixture while heating to a temperature of 50° C. Agitated the mixture at 50° C. for 15 min (making sure all the material was in solution), then added 114 mL (1.2 moles) of p-fluoroaniline slowly via the addition funnel (exothermic reaction). After the addition was complete, agitated the thick slurry for 1 hr at 50° C., cool to r.t. and agitated for 30 min, Filtered the product, washed the cake with 150 mL of isopropanol, dried the wet cake in a draft oven at 50° C. for 24 h or until dry to yield 222 g of the imine (88%); mp: 180-182° C.

Process Example

Step (a)

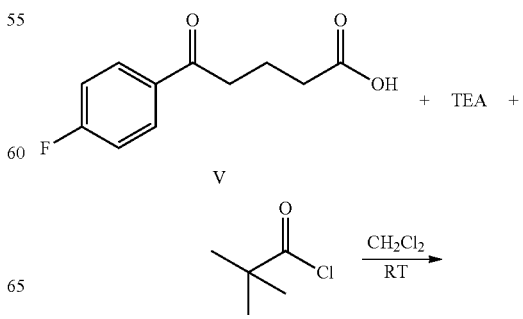

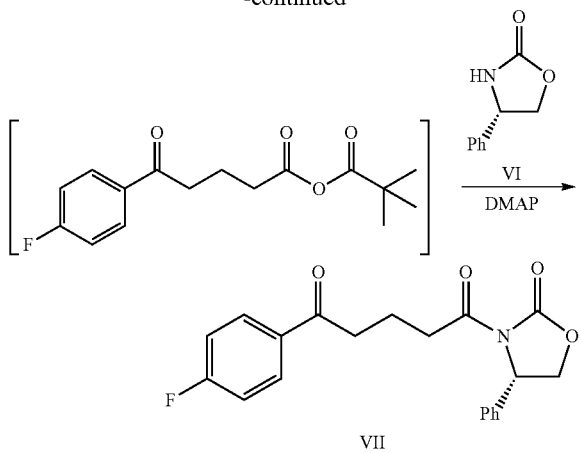

Equipped a 3-necked 500 mL round bottom flask with a thermometer, an addition funnel and a nitrogen inlet. Added p-fluoro-benzoylbutyric acid (20 g, 95.15 mmol), CH$_2$Cl$_2$ (100 mL) and TEA (23 mL, 165 mmol) and agitated the mixture at room temperature for 5 min. Added trimethylacetyl chloride (11.3 mL, 91.75 mmol) slowly over a period of 30 min, Checked for complete formation of mixed anhydride by NMR.

Added the compound of Formula VI (10 g, 61.3 mmol), DMAP (1.6 g, 13 mmol) and dry DMF (10 mL) and heated the mixture at reflux for about 7 h or until the reaction was complete (<3% compound III) by NMR. Cooled to room temperature, transferred the batch to a flask containing 2N H$_2$SO$_4$ (80 mL) slowly with agitation and continued agitation for about 30 min. Separated the layers and washed the organic layer with 5% NaHCO$_3$ (80 mL).

Concentrated the organic layer and crystallized the product from isopropyl alcohol (100 mL), filtered and dried. Yield: 20 g (92% molar); mp: 92-94° C.

Step (b)

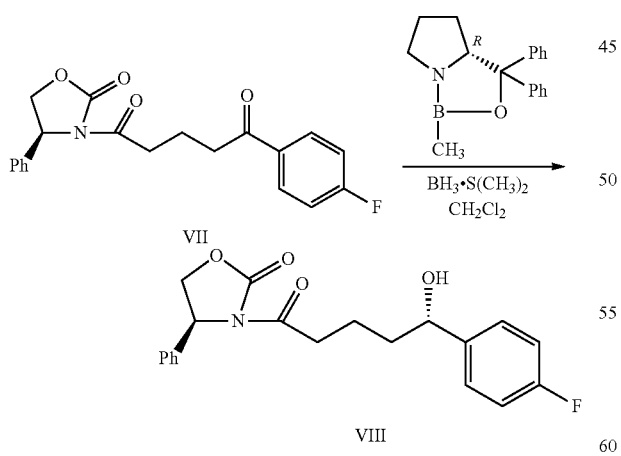

Equipped a 3-necked 250 mL round bottom flask with a thermometer, an addition funnel and a nitrogen inlet, Added dry CH$_2$Cl$_2$ (20 mL) and neat borane dimethyl sulfide (2.82 mL, 28.2 mmol) and cooled the mixture to −5° to 0° C. Added a previously prepared toluene solution of (R)-tetrahydro-1-methyl-3,3-diphenyl-1H,3H-pyrrolo(1,2-c)(1,3,2) oxazaborolidine (1.4 mL, 1.4 mmol, 5 mole %) to the mixture and stirred for 15 min. at <0° C. Added a solution of compound VII (10 g, 28.1 mmol) in CH$_2$Cl$_2$ (30 mL) slowly over a period of 3-4 h and maintained the reaction temperature between −5° to 0° C. Continued stirring for 1 to 2 h or until the reaction completed (<0.1% compound VII) by NMR. Quenched the reaction by slowly adding CH$_3$OH (4 mL) while maintaining the temperature <0° C. Added 5% hydrogen peroxide (20 mL) followed by 4N H$_2$SO$_4$ (1.5 mL). Agitated the mixture for 15 min., separated the organic layer and washed with 2N H$_2$SO$_4$ (20 mL), 5% Na$_2$SO$_3$ (50 mL) and 10% NaCl (50 mL). Concentrated the organic layer to a low volume until water content is <0.05%. The product was used directly in the next step. Solution yield: >95%; de: 98%.

Step (c)

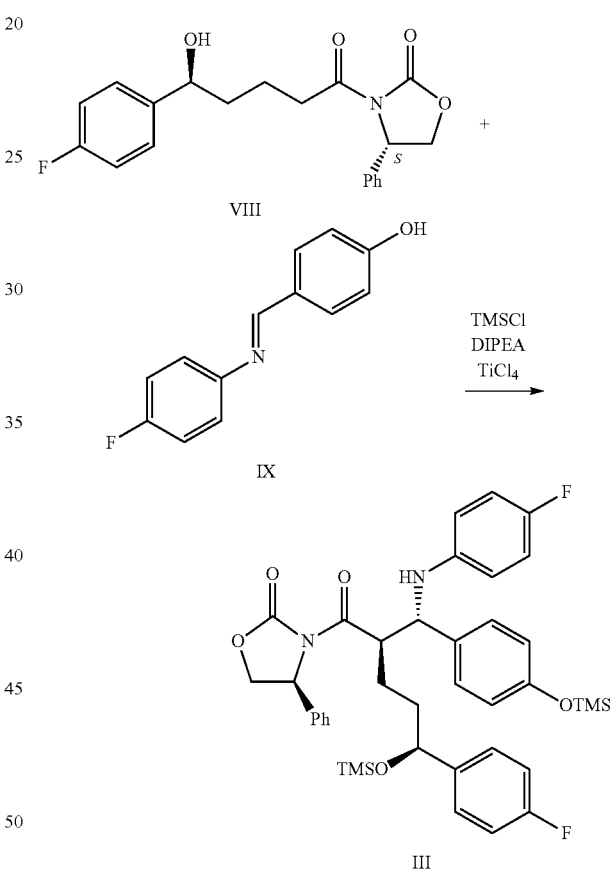

Equipped a 3-necked 500 mL round bottom flask with a thermometer, an addition funnel and a nitrogen inlet. Added the CH$_2$Cl$_2$ solution of compound VIII (10 g equivalent of compound VIII, 28.1 mmol) from step (b) and compound IX (12.05 g) and adjusted the total volume of the reaction mixture to 150 mL with dry CH$_2$Cl$_2$. Cooled the mixture to −10° C. and slowly added DIPEA (25.7 mL, 147.5 mmol) and maintained the temperature at <−5° C. Added TMSCl (13.5 mL, 92.3 mmol) over a period of 30 min. while maintaining the reaction temperature <−5° C. Agitated the reaction for 1 h or until the silylation was judged complete by NMR. Lowered the reaction temperature to −25 to −30° C. Added TiCl$_4$ (3.4 mL, 30.8 mmol) slowly and maintained the temperature <−25° C. Agitated the reaction for 3 h at <−25° C. and checked the reaction completion by NMR. Added glacial acetic acid (8 mL) slowly to the reaction mixture while maintaining the reaction temperature between −25 and −30° C. Poured the reaction mixture into 7% aqueous tartaric acid solution (140 mL) at 0° C., agitate for 1-2 h, and allowed the temperature to gradually rise to room temperature. Added 20% aqueous NaHSO$_3$ solution (50 mL) and continued agitation for another 2 h. Separated the organic layer and wash with water (120 mL). Concentrated the organic layer to a low volume and added bistrimethylsilyl acetamide (8.4 mL) and heated the mixture to reflux for 30 min. Concentrated the mixture to remove CH$_2$Cl$_2$ and crystallized the product from an ethyl acetate and heptane mixture, filtered, washed and dried to give 13 g (65% molar yield from compound VIII) of compound III. $^1$H NMR (CDCl$_3$, 400 MHz) δ 7.18 (7H, m), 7.06 (2H, t, J=7.6 Hz), 6.98 (2H, t, J=8.66 Hz), 6.77 (4H, m), 6.43 (2H, dd, J=8.84, 4.4 Hz), 5.43 (1H, dd, J=8.13, 2.21 Hz), 4.47 (1H, t, J=8.57 Hz), 4.46 (2H, m), 4.29 (1H, d, J=9.51 Hz), 4.21 (1H, dd, J=8.71, 2.91 Hz), 1.55 (3H, m), 1.41 (1H, m), 0.28 (9H, s), −0.07 (9H, s).

Step (d)

Example 1

Intramolecular Cyclization of Compound III with Tetrabutylammonium Acetate

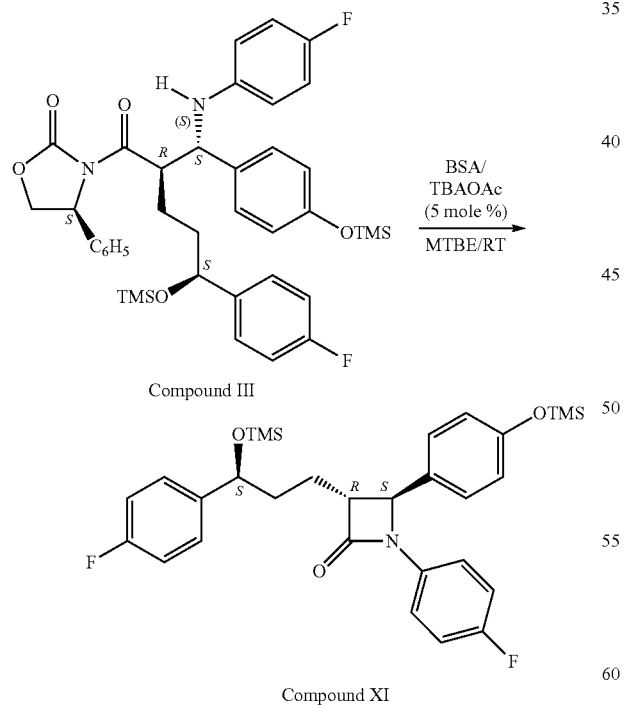

Compound III

Compound XI

Equipped a 1-necked 50 mL round bottom flask with a magnetic stirrer and a stopper. Added Compound III (1.0 g, 1.4 mmol), N,O bis(trimethylsilyl)acetamide (1.0 mL), tetrabutylammonium acetate (0.020 g, 0.066 m mole or 5 mole %) and methyl t-butyl ether (10 mL). Stirred the mixture at room temperature for about 15 minutes. Analysis of the reaction mixture by $^1$H NMR (CDCl$_3$, 400 MHz) indicated the disappearance of compound III (specifically the disappearance of a characteristic doublet of a doublet at δ 6.43 ppm and appearance of a doublet of a triplet at 3.04 ppm (J=7.51, 2.2 Hz) and a doublet at 4.54 (J=2.2 Hz). These two peaks are characteristic for C-3 and C-4 protons of a trans β-lactam respectively. HPLC analysis of an acidified sample of the reaction mixture also gave a peak at 21.2 min (96% area) matching the retention time of an authentic sample of compound XI.

Example 2

Intramolecular Cyclization of Compound III with Potassium Acetate and Tetrabutylammonium Bromide

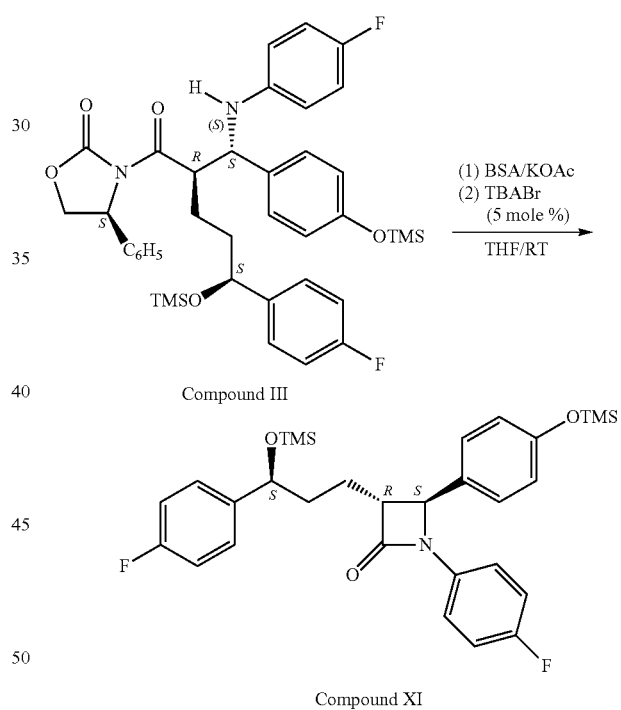

Compound III

Compound XI

Equipped a 3-necked 125 mL round bottom flask with a magnetic stirrer. Added Compound III (5 g, 7.0 mmol), N,O-bis(trimethylsilyl)acetamide (5.0 mL), potassium acetate (0.035 g, 0.36 m mole or 5 mole %), and tetrahydrofuran (50 mL), Stirred the mixture at room temperature for 0.5 h. Checked reaction progress by $^1$HNMR which indicated no reaction whatsoever. Added tetrabutylammonium bromide (0.112 g, 0.35 mmol or 5 mole %). Stirred the mixture at room temperature for 0.7 h. Analysis of the reaction mixture by $^1$H NMR was conducted in the same manner as for Example 1 above.

Example 3

Intramolecular Cyclization of Compound III with Cesium Fluoride and Tetrabutylammonium Bromide

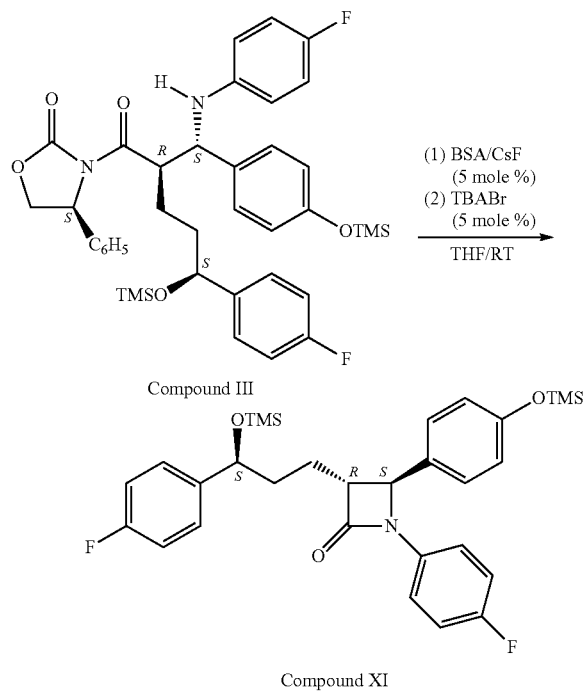

Compound III (1) BSA/CsF (5 mole %)
(2) TBABr (5 mole %)
THF/RT

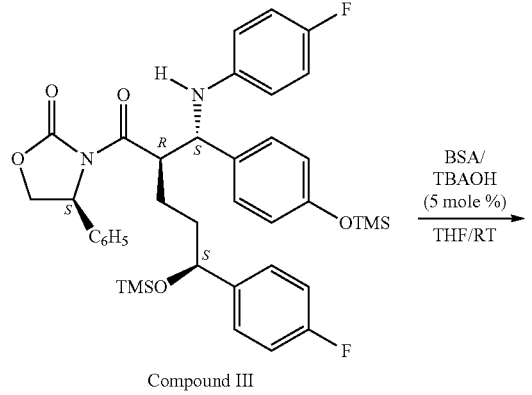

Compound XI

Equipped a 3-necked 250 mL round bottom flask with a thermometer, an addition funnel and a nitrogen inlet. Added Compound III (5 g, 6.97 mmol), and anhydrous Tetrahydrofuran (50 mL). Stirred the mixture at room temperature for about 10 minutes, or until all solids dissolved. Added N,O Bistrimethylsilylacetamide (BSA, 5 mL, 20.2 mmol). Stirred the solution at room temperature for about 15 minutes. Added Cesium Flouride (CsF, 52.9 mg, 0.35 mmol, 5 mole %). Stirred the mixture at room temperature for about 45 minutes. Charged tetra-N-Butylammonium Bromide (TBABr, 112 mg, 0.35 mmol, 5 mole %). Stirred the mixture at room temperature for about 1 hour. Analysis of the reaction mixture by $^1$H NMR was conducted in the same manner as for Example 1 above.

Example 4

Intramolecular Cyclization of Compound III with Tetrabutylammonium Hydroxide Compound III BSA/TBAOH (5 mole %)
THF/RT

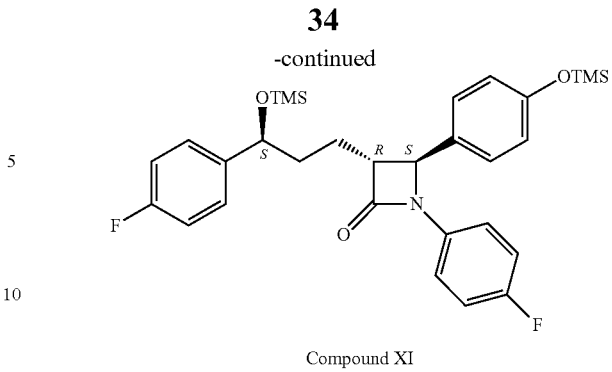

Compound XI

Equipped a 1-necked 50 mL round bottom flask with a magnetic stirrer and a stopper. Added compound III (1.0 g, 1.4 mmol), N,O-bis(trimethylsilyl) acetamide (1.0 mL), and tetrahydrofuran (10 mL). Stirred the mixture at room temperature for about 10 minutes. Added aqueous solution of tetrabutylammonium hydroxide (0.05 mL; 40 w/w %; 0.077 mmole or 5.5 mole %). Stirred the mixture at room temperature for 1.3 h. Analysis by $^1$HNMR showed that the reaction was only half way to completion. Added more N,O-bis(trimethylsilyl) acetamide (1.0 mL). Stirred the mixture at room temperature for 1 h. Analysis of the reaction mixture by $^1$H NMR was conducted in the same manner as for Example 1 above.

Example 5

Intramolecular Cyclization of Compound III with Potassium Acetate

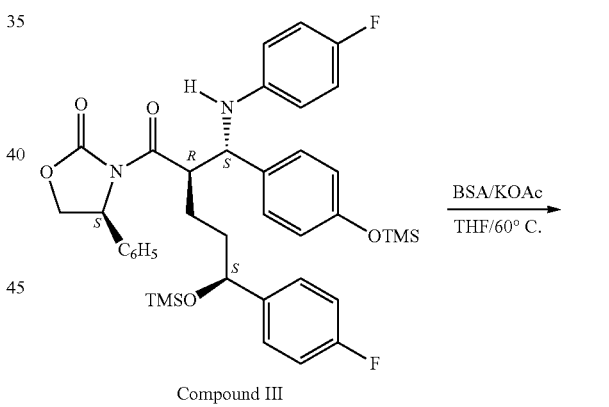

Compound III

BSA/KOAc
THF/60° C.

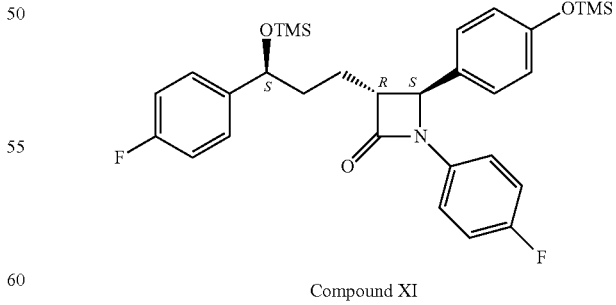

Compound XI

Equipped a 1-necked 50 mL round bottom flask with a magnetic stirrer and a stopper. Added compound III (1.0 g, 1.4 mmol), N,O-bis(trimethylsilyl)acetamide (1.0 mL), potassium acetate (0.14 g, 1.4 mmol), and tetrahydrofuran (10 mL). Stirred the mixture at room temperature for about 1.5 h.

Analysis by $^1$HNMR showed no reaction. Heated the mixture to about 50° C., and stirred the mixture at that temperature for about 3 h. Analysis by $^1$HNMR showed that the reaction was only about 65% complete. Again, heated the mixture to about 60° C., and stirred the mixture at that temperature for about 1 h. Analysis of the reaction mixture by $^1$H NMR was conducted in the same manner as for Example 1 above.

Step (e)

Added a premixed solution of isopropyl alcohol and 2N $H_2SO_4$ to the product of step (d) and agitated the mixture at room temperature for 1 h. Crystallized compound IV from aqueous isopropyl alcohol. Filtered the product and washed with dilute aqueous isopropyl alcohol followed by water until the pH of wash was <5. Dried the product at 60° C. in a draft oven or under vacuum to give compound IV.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Therefore, we claim:

1. A process for preparing an azetidinone compound represented by the structural Formula (I):

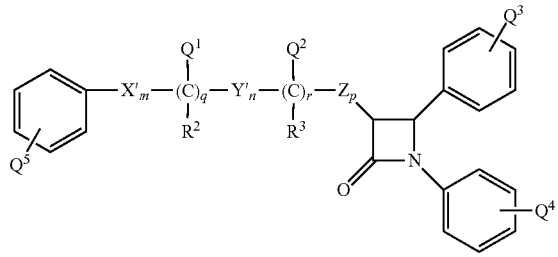

(I)

or pharmaceutically acceptable salts or solvates thereof, comprising the steps of:
(1) reacting a β-(substituted-amino) compound of Formula (II)

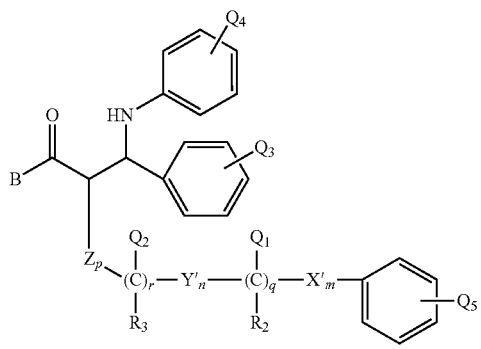

(II)

with
at least one silylating agent and
at least one cyclizing agent which is (a) selected from the group consisting of an alkali metal carboxylate, quaternary ammonium carboxylate, quaternary ammonium hydroxide quaternary ammonium alkoxide, quaternary ammonium aryloxide and hydrates of any of the foregoing, or
(b) the reaction product of:
  (i) at least one quaternary ammonium halide and at least one alkali metal carboxylate; or
  (ii) at least one quaternary ammonium chloride, quaternary ammonium bromide, or quaternary ammonium iodide and at least one alkali metal fluoride,
wherein the quaternary ammonium moiety of the cyclizing agent is substituted by four groups independently selected from the group consisting of alkyl arylalkyl and arylalkyl-alkyl;

and (2) if one or more or $R^6$, $R^7$ and $R^8$ is a protecting group, optionally removing the one or more protecting groups from the product of step 1;

wherein:
X', Y' and Z can be the same or different and each is independently selected from the group consisting $—CH_2—$, $—CH(alkyl)-$ and $—C(alkyl)_2-$;

$Q^1$ and $Q^2$ can be the same or different and each is independently selected from the group consisting of H, G, $—(C_1-C_{30}$ alkylene)-G, $—OR^6$, $—OC(O)R^6$, $—OC(O)OR^9$, and $—OC(O)NR^6R^7$;

$Q^3$, $Q^4$, and $Q^5$ can be the same or different and each is independently 1 to 5 substituents independently selected from the group consisting of acyl, alkyl, alkylaryl, alkylheteroaryl, alkylsulfonyl alkenyl, alkoxy, alkoxycarbonyl, alkynyl, -G, $—(C_1-C_{30}$ alkylene)-G, $—OR^6$,
$—(C_1-C_{10}$ alkylene)-$OR^6$, $—C(O)R^6$, $—(C_1-C_{10}$ alkylene)-$C(O)R^6$,
$—C(O)OR^6$, $—(C_1-C_{10}$ alkylene)-$C(O)OR^6$, $—OC(O)R^6$, $—(C_1-C_{10}$ alkylene)-$—OC(O)R^6$, $—OC(O)OR^9$, $—(C_1-C_{10}$ alkylene)-$OC(O)OR^9$,
$—CH=CH—C(O)R^6$, $—CH=CH—C(O)OR^6$, $—C≡C—C(O)OR^6$, $—C≡C—C(O)R^6$,
$—O—(C_1-C_{10}$ alkylene)-$OR^6$, $—O—(C_1-C_{10}$ alkylene)-$C(O)R^6$,
$—O—(C_1-C_{10}$ alkylene)-$C(O)OR^6$, $—CN$, $—C(=N—CN)—NH_2$, $—C(=NH)—NHR^{10}$,
$—O—(C_1-C_{10}$ alkylene)-$C(O)NR^6R^7$,
$—O—C(O)NR^6NR^7C(O)OR^6$,
$—O—(C_1-C_{10}$ alkylene)-$C(O)NH^6NR^7C(O)OR^6$,
$—OC(O)—(C_1-C_{10}$ alkylene)-$C(O)OR^6$,
$—C(O)NR^6R^7$, $—(C_1-C_{10}$ alkylene)-$C(O)NR^6R^7$,
$—OC(O)NR^6R^7$, $—(C_1-C_{10}$ alkylene)-$OC(O)NR^6R^7$, $—NO_2$, $—NR^6R^7$, $—(C_1-C_{10}$ alkylene)-$NR^6R^7$, $—O—(C_2-C_{10}$ alkylene)-$NR^6R^7$, $—NR^6C(O)R^7$,
(a) a deprotonated chiral auxiliary selected from the group consisting of

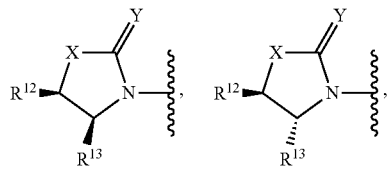

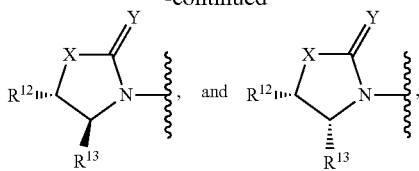

wherein X is —O—, —S— or —N($C_1$-$C_6$ alkyl)-, Y is O or S; $R^{12}$ and $R^{13}$ are each independently selected from the group consisting of alkyl, alkoxycarbonyl, phenyl, naphthyl, benzyl, substituted phenyl, substituted naphthyl and substituted benzyl, wherein the substituents on the phenyl, naphthyl or benzyl are 1-3 substituents selected from the group consisting of alkyl, alkoxy, phenyl and benzyl; or wherein one of $R^{12}$ or $R^{13}$ is as defined above and the other is hydrogen, (b) ($R^{14}$)($R^{15}$)N—, wherein $R^{14}$ and $R^{15}$ are each independently alkyl, aryl or arylalkyl,
(c) $R^{14'}$—O—, and
(d) $R^{14'}$—S—;
$R^{14'}$ is alkyl or aryl;
and wherein
alkyl, independently at each occurrence, is optionally substituted with one or more substituents independently selected from the group consisting of halo, aryl, cycloalkyl, cyano, hydroxy, alkoxy, alkylthio, amino, —NH(alkyl), —NH(cycloalkyl), —N(alkyl)$_2$ which alkyls can be the same or different, carboxy and —C(O)O-alkyl;
alkenyl and alkynyl, independently at each occurrence, are each optionally substituted with one or more substituents independently selected from the group consisting of halo, alkyl, aryl, cycloalkyl, cyano, heteroaryl, and alkoxy;
aryl, cycloalkyl, cycloalkenyl, heteroaryl and heterocyclyl, independently at each occurrence, are each optionally substituted with one or more ring system substituents, wherein each ring system substituent is independently selected from the group consisting of:
a) alkyl, alkenyl, alkynyl, aryl, heteroaryl, aralkyl, alkylaryl, aralkenyl, heteroaralkyl, heteroarylalkynyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, —C(=N—CN)—NH$_2$, —C(=NH)—NH$_2$, —NR$^6$C(O)OR$^9$, —NR$^6$C(O)NR$^7$R$^8$, —NR$^6$S(O)$_{0-2}$R$^9$, —N(S(O)$_{0-2}$R$^9$)$_2$, —CHNOR$^6$, —C(O)NR$^6$R$^7$, —C(O)NR$^6$NR$^6$R$^7$, —S(O)$_{0-2}$NR$^6$R$^7$, —S(O)$_{0-2}$R$^9$, —O—C(O)—($C_1$-$C_{10}$ alkylene)-C(O)NR$^6$R$^7$, —OC(O)—($C_1$-$C_{10}$ alkylene)-NR$^6$C(O)O-(alkylaryl), —P(O)(OR$^{10}$)$_2$, —($C_1$-$C_{10}$ alkylene)-OSi(alkyl)$_3$, —CF$_3$, —OCF$_3$, halo, alkoxyalkoxy, alkoxyalkoxyalkoxy, alkoxycarbonylalkoxy, alkoxyarylalkoxy, alkoxyiminoalkyl, alkyldioyl, allyl, allyloxy, aryloxycarbonyl, aryl, arylalkyl, aryloxy, arylalkoxy, aroyl, aroyloxy, arylsulfonyl, aroylaroyloxy, aroyl, arylalkoxycarbonyl, benzoylbenzoyloxy, carboxy, cyano, cycloalkyl, cycloalkylalkyl, cycloalkenyl, cycloalkenylalkyl, heteroaryl, heteroarylalkenyl, heteroarylalkynyl, heteroarylalkyl, heteroarylalkoxy, heteroarylsulfornyl, heteroarylthio, dioxolanyl, heterocyclyl, heterocyclylalkyl, heterocyclylcarbonyl, heterocyclylcarbonylalkoxy, hydroxy, hydroxyalkyl, and alkylsulfonyl;

wherein optionally one or more carbon atoms of the —($C_1$-$C_{30}$ alkylene)- radical of $Q^1$, $Q^2$, $Q^3$, $Q^4$ and $Q^5$ is independently replaced by
—O—, —C(O)—, —CH=CH—, —C≡C—, —N(alkyl)-, —N(alkylaryl)- or —NH—;

G is selected from the group consisting of a sugar residue, disugar residue, trisugar residue, tetrasugar residue, sugar acid amino sugar, an amino acid residue which may be attached at an acid, amine or carbon portion of the amino acid residue, an oligopeptide residue comprising 2 to 9 amino acids, and —S(O)$_2$—OH;

$R^2$ and $R^3$ can be the same or different and each is independently selected from the group consisting of hydrogen, alkyl and aryl;

$R^6$, $R^7$ and $R^8$ can be the same or different and each is independently selected from the group consisting of hydrogen, alkyl, cycloalkyl, aryl, arylalkyl and a protecting group;

each $R^9$ is independently alkyl, cycloalkyl, aryl or arylalkyl, each $R^{10}$ is independently H or alkyl;

q is 0 or 1;

r is 0 or 1; and m, n and p are independently selected from 0, 1, 2, 3 or a provided that at least one of q and r is 1, and the sum of m, n, p, q and r is 1, 2, 3, 4, 5 or 6; and provided that when p is 0 and r is 1, the sum of in, q and n is 1, 2, 3, 4 or 5; and B is selected from the group consisting of: —C(=NH)—NH(alkyl), $Y_1Y_2$N—, $Y_1Y_2$N-alkyl-, $Y_1Y_2$NC(O)—, $Y_1Y_2$NSO$_2$— and —SONY$_1Y_2$, wherein $Y_1$ and $Y_2$ may be the same or different and are independently selected from the group consisting of hydrogen, alkyl, aryl, and cycloalkyl, and aralkyl, and b) a single moiety which simultaneously replaces two available hydrogens on two adjacent carbon atoms selected from methylene dioxy, ethylenedioxy and —C(CH$_3$)$_2$—.

2. The process according to claim 1, wherein $Q^1$ is —OR$^6$, $Q^3$ is —OR$^6$ and $R^6$ is a protecting group in Formula II, and the protecting groups are removed from the product of step 1 to produce the compound represented by the structural Formula (IV) or a pharmaceutically acceptable salt or solvate thereof:

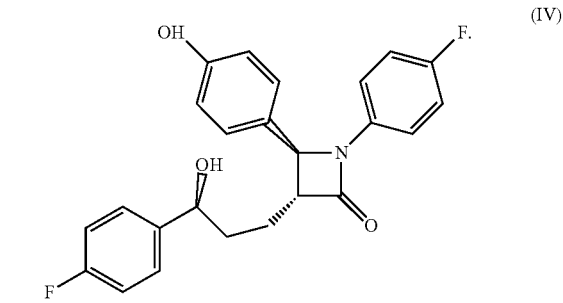 [SMILES: O=C1[C@H](CC[C@H](O)c2ccc(F)cc2)[C@@H](c2ccc(O)cc2)N1c1ccc(F)cc1]

(IV)

3. The process according to claim 1, wherein B is a deprotonated chiral auxiliary selected from the group consisting of

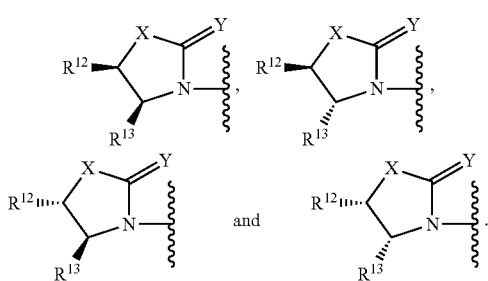

4. The process according to claim 3, wherein the aryl group of $R^{12}$ or $R^{13}$ is independently selected from the group consisting of phenyl, naphthyl, benzyl, substituted phenyl, substituted naphthyl and substituted benzyl, wherein the substituents on the phenyl, naphthyl or benzyl are 1-3 substituents selected from the group consisting of alkyl, alkoxy, phenyl and benzyl.

5. The process according to claim 1, wherein B is $(R^{14})(R^{15})N-$.

6. The process according to claim 3, wherein in the compound of Formula II, $Q^1$ is $-OR^6$, $Q^3$ is $-OR^6$ and $R^6$ is a protecting group, and the protecting groups are removed from die product of step 1 to produce the compound represented by the structural Formula (IV):

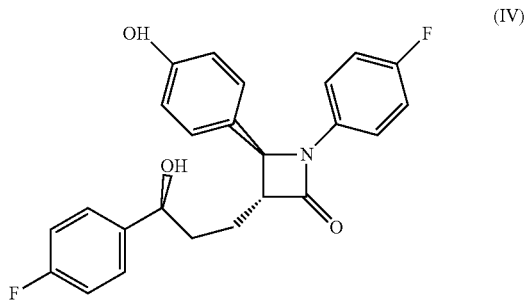 [SMILES: O=C1[C@H](CC[C@H](O)c2ccc(F)cc2)[C@@H](c2ccc(O)cc2)N1c1ccc(F)cc1]

or a pharmaceutically acceptable salt or solvate thereof.

7. The process according to claim 6, wherein the compound of Formula (II) is represented by Formula (III):

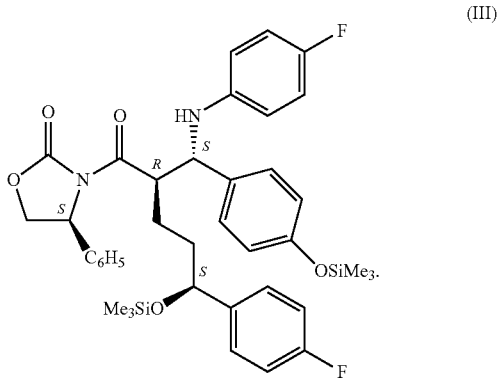

8. The process according claim 1, wherein B is $R^{14'}-O-$.
9. The process according claim 1, wherein B is $R^{14'}-S-$.
10. The process according to claim 1, wherein the silylating agent is a sylylenol ether.

11. The process according claim 10, wherein the silylating agent is selected from the group consisting of bistrimethylsilylacetamide, N-methyl-O-trimethyl silylacetamide or isopropenyloxy trimethylsilane.

12. The process according to claim 1, wherein the alkali metal carboxylate is a carboxylate salt of an alkali metal selected from the group consisting of lithium, sodium, potassium and cesium.

13. The process according to claim 1, wherein the alkali metal carboxylate or quaternary ammonium carboxylate comprises a carboxylate moiety selected from the group consisting of formate, acetate, propionate, butyrate, valerate, caproate, caprylate, laurate, myristate, palmitate, stearate, oleate, linoleate, linolenate, cyclohexanecarboxylate, phenylacetate, benzoate and toluate.

14. The process according to claim 13, wherein the carboxylate moiety of the alkali metal carboxylate is acetate.

15. The process according to claim 13, wherein the alkali metal carboxylate is potassium acetate.

16. The process according to claim 13, wherein the carboxylate moiety of the quaternary ammonium carboxylate is acetate.

17. The process according to claim 1, wherein the quaternary ammonium moiety of the cyclizing agent is tetra n-butylammonium.

18. The process according to claim 13, wherein the quaternary ammonium carboxylate is tetra n-butylammonium acetate.

19. The process according to claim 1, wherein the quaternary ammonium hydroxide, is tetra n-butylammonium hydroxide.

20. The process according to claim 1, wherein the quaternary ammonium halide comprises a halide moiety selected from the group consisting of fluoride, chloride, bromide and iodide.

21. The process according to claim 1, wherein the cyclizing agent is the reaction product of tetra n-butylammonium bromide and potassium acetate.

22. The process according to claim 1, wherein the cyclizing agent is the reaction product of tetra n-butylammonium bromide and cesium fluoride.

23. The process according to claim 1, wherein the at least one cyclizing agent which is the reaction product of (b) is formed in situ in the presence of the β-(substituted-amino) compound of Formula (II) and the at least one silylating agent.

24. The process according to claim 1, further comprising the step of forming the at least one cyclizing agent which is the reaction product of (b) prior to reaction with the β-(substituted-amino) compound of Formula (II) and the at least one silylating agent.

25. The process according to claim 1 wherein the silylating agent is bistrimethylsilylacetamide and the cyclizing agent is tetra n-butylammonium acetate.

26. The process according to claim 1, further comprising adding a second cyclizing agent which is a fluoride ion catalyst.

27. The process according to claim 1, comprising the steps or (A) reacting the compound of Formula (II) with at least one silylating agent, followed by (B) reacting the product of step (A) with at least one cyclizing agent.

28. The process according to claim 1 for preparing an azetidinone represented by the structural Formula (IV) or a pharmaceutically acceptable salt or solvate thereof:

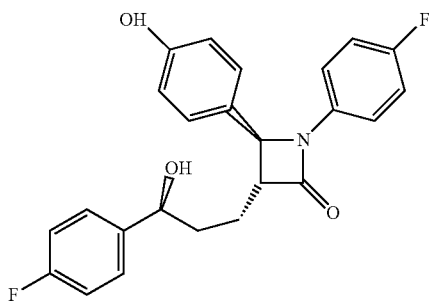

comprising reacting:
(1) a β-(substituted-amino) compound of Formula (II) having the Formula (III)

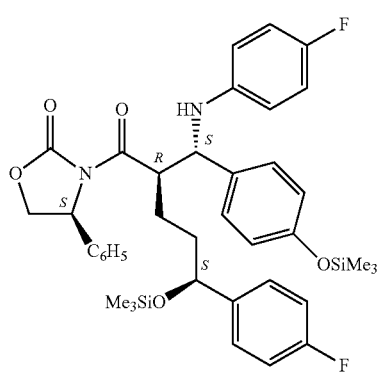

with the at least one silylating agent and
the at least one cyclizing agent;
and (2) removing the SiMe$_3$ protecting groups from the product of Step 1.

29. A process for preparing a compound represented by the Formula (IV) or a pharmaceutically acceptable salt or solvate thereof:

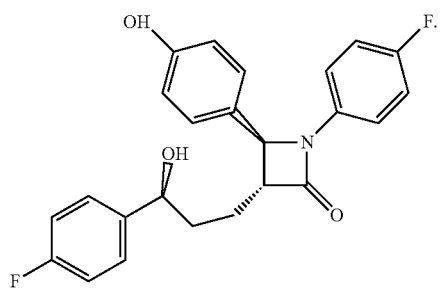

comprising the steps of:
cyclizing the β-(substituted-amino) compound of Formula XII

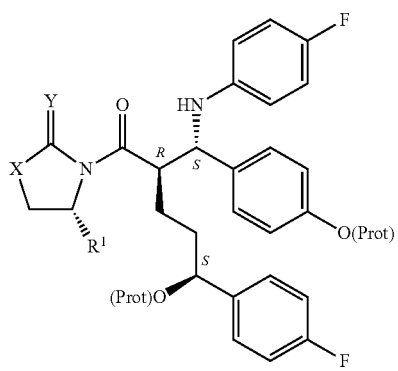

wherein X is —O—, —S— or —N(C$_1$-C$_6$ alkyl); Y is =O or =S; R$^1$ is selected from the group consisting of alkyl, alkoxycarbonyl, phenyl, naphthyl, benzyl, substituted phenyl, substituted naphthyl and substituted benzyl, wherein the substituents on the phenyl, naphthyl or benzyl are 1-3 substituents selected from the group consisting of alkyl, alkoxy, phenyl and benzyl; and Prot is it silyl protecting group;
with at least one silylating agent and at least one cyclizing agent which is:
(a) selected from the group consisting of an alkali metal carboxylate, quaternary ammonium carboxylate, quaternary ammonium hydroxide, quaternary ammonium alkoxide, quaternary ammonium aryloxide and hydrates of any of the foregoing; or
(b) the reaction product of
(i) at least one quaternary ammonium halide and at least one alkali metal carboxylate; or
(ii) at least one quaternary ammonium chloride, quaternary ammonium bromide, or quaternary ammonium iodide and at least one alkali metal fluoride,
wherein a quaternary ammonium moiety of the cyclizing agent is substituted by four groups independently selected from the group consisting of optionally substituted alkyl, arylalkyl and arylalkyl-alkyl,
to obtain the compound of Formula XI:

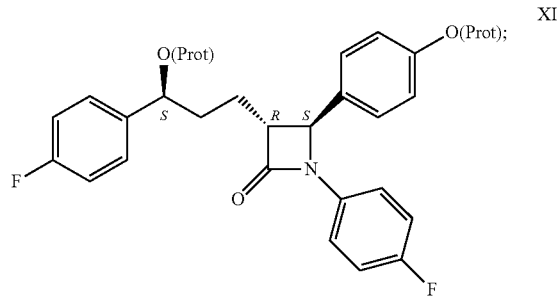

and
removing the silyl protecting groups to form the compound of Formula (IV) or a pharmaceutically acceptable salt or solvate thereof.

30. The process according to claim 29, further comprising the steps of:

reacting a chiral alcohol of Formula VIII, an imine Formula IX and a silyl protecting agent, then condensing the silyl-protected compounds to obtain the β-(substituted-amino) compound of Formula XII:

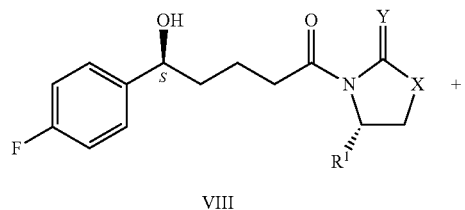

VIII

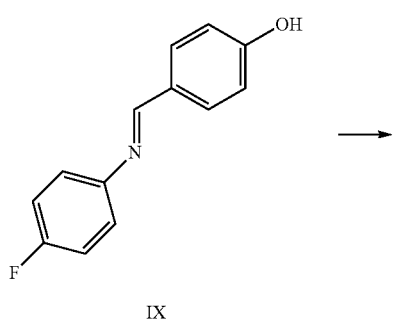

IX

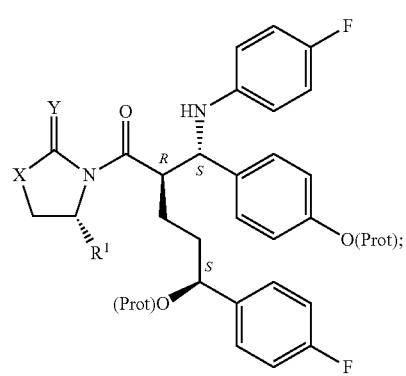

XII prior to cyclizing the compound of Formula XII.

31. The process according to claim 29, further comprising the steps of:

(a) reacting p-fluorobenzoylbutyric acid of Formula V with pivaloyl chloride then reacting the product thereof with a chiral auxiliary of Formula VI to obtain a ketone of Formula VII:

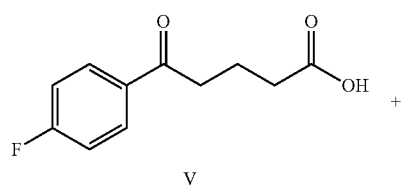

V

-continued

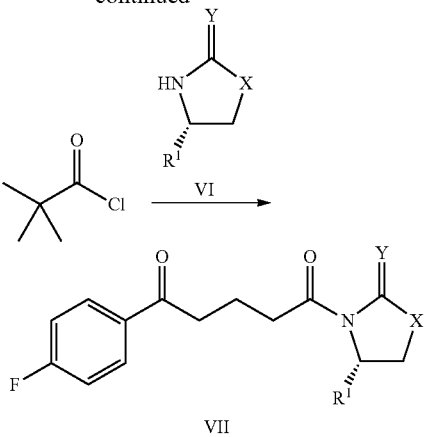

VII (b) reducing the ketone of Formula VII in the presence of a chiral catalyst to an alcohol of Formula VIII:

VII

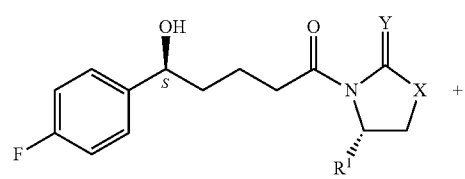

VIII (c) reacting the chiral alcohol of Formula VIII, an imine of Formula IX and a silyl protecting agent, then condensing the silyl-protected compounds to obtain a β-(substituted-amino)amide Formula XII, wherein Prot is a silyl protecting group:

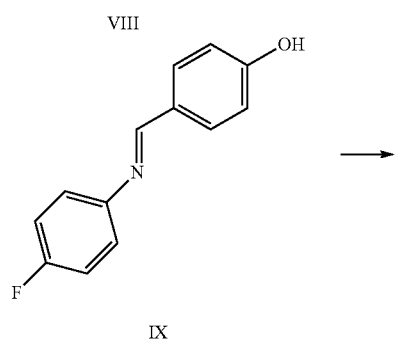

VIII

IX

-continued

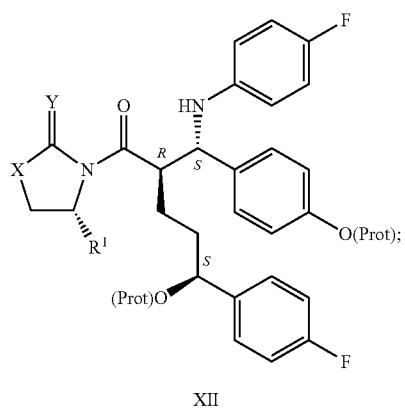

XII prior to cyclizing the compound of Formula XII.

32. The process according to claim 29 wherein the at least one cyclizing agent is:

(a) selected from the group consisting of an alkali metal carboxylate, quaternary ammonium carboxylate, quaternary ammonium hydroxide, quaternary ammonium alkoxide, quaternary ammonium aryloxide and hydrates of any of the foregoing; or (b) the reaction product of:
at least one quaternary ammonium halide which is a quaternary ammonium bromide, chloride, or iodide and at least one alkali metal carboxylate;

wherein a quaternary ammonium moiety of the cyclizing agent is substituted by four groups independently selected from the group consisting of alkyl, arylalkyl and arylalkyl-alkyl.

* * * * *